United States Patent
Borer et al.

(10) Patent No.: US 7,718,784 B2
(45) Date of Patent: May 18, 2010

(54) SWITCHABLE NUCLEIC ACIDS FOR DIAGNOSTICS, SCREENING AND MOLECULAR ELECTRONICS

(75) Inventors: Philip N. Borer, Chittenango, NY (US); Bruce S. Hudson, Syracuse, NY (US); Christopher L. DeCiantis, Durham, NC (US)

(73) Assignee: Syracuse University, Syracuse, NY (US)

(*) Notice: Subject to any disclaimer, the term of this patent is extended or adjusted under 35 U.S.C. 154(b) by 113 days.

(21) Appl. No.: 10/544,591

(22) PCT Filed: Feb. 3, 2004

(86) PCT No.: PCT/US2004/003002

§ 371 (c)(1),
(2), (4) Date: Jan. 6, 2006

(87) PCT Pub. No.: WO2004/069850

PCT Pub. Date: Aug. 19, 2004

(65) Prior Publication Data

US 2006/0216692 A1     Sep. 28, 2006

Related U.S. Application Data

(60) Provisional application No. 60/445,090, filed on Feb. 4, 2003.

(51) Int. Cl.
  *C07H 21/02*   (2006.01)
  *C07H 21/04*   (2006.01)
  *C12Q 1/68*    (2006.01)

(52) U.S. Cl. .............. 536/23.1; 536/24.2; 536/24.3

(58) Field of Classification Search ............ None
See application file for complete search history.

(56) References Cited

U.S. PATENT DOCUMENTS

| | | | |
|---|---|---|---|
| 5,312,728 A | * | 5/1994 | Lizardi et al. ............. 435/6 |
| 5,496,938 A | | 3/1996 | Gold et al. |
| 5,786,462 A | | 7/1998 | Schneider et al. |
| 5,821,046 A | | 10/1998 | Karn et al. |

(Continued)

FOREIGN PATENT DOCUMENTS

WO     WO 99/31276      6/1999

(Continued)

OTHER PUBLICATIONS

Jose, A.M. et al., Nucl. acids Res., vol. 29, pp. 1631-1637 (2001).*

(Continued)

*Primary Examiner*—Teresa E Strzelecka
(74) *Attorney, Agent, or Firm*—Knobbe, Martens, Olson & Bear, LLP

(57) ABSTRACT

In one embodiment, the present invention relates to fluorescent nucleic acid constructs and methods of using these switchable constructs to rapidly screen for target molecule interactions. More particularly, an RNA/DNA chimera comprising a fluorophore-quencher pair and a nucleic acid construct is disclosed for the rapid screening of interactions between the HIV-1 nucleocapsid protein, NCp7, and a stem-loop region, SL3, of the HIV-1 RNA, or antagonists thereof. The compositions and methods disclosed herein can be used in preferred aspects of the present invention for diagnosing disease states, distinguishing the presence of infectious or toxic agents, drug discovery and design, and molecular electronic applications.

30 Claims, 8 Drawing Sheets

U.S. PATENT DOCUMENTS

Figure 1:
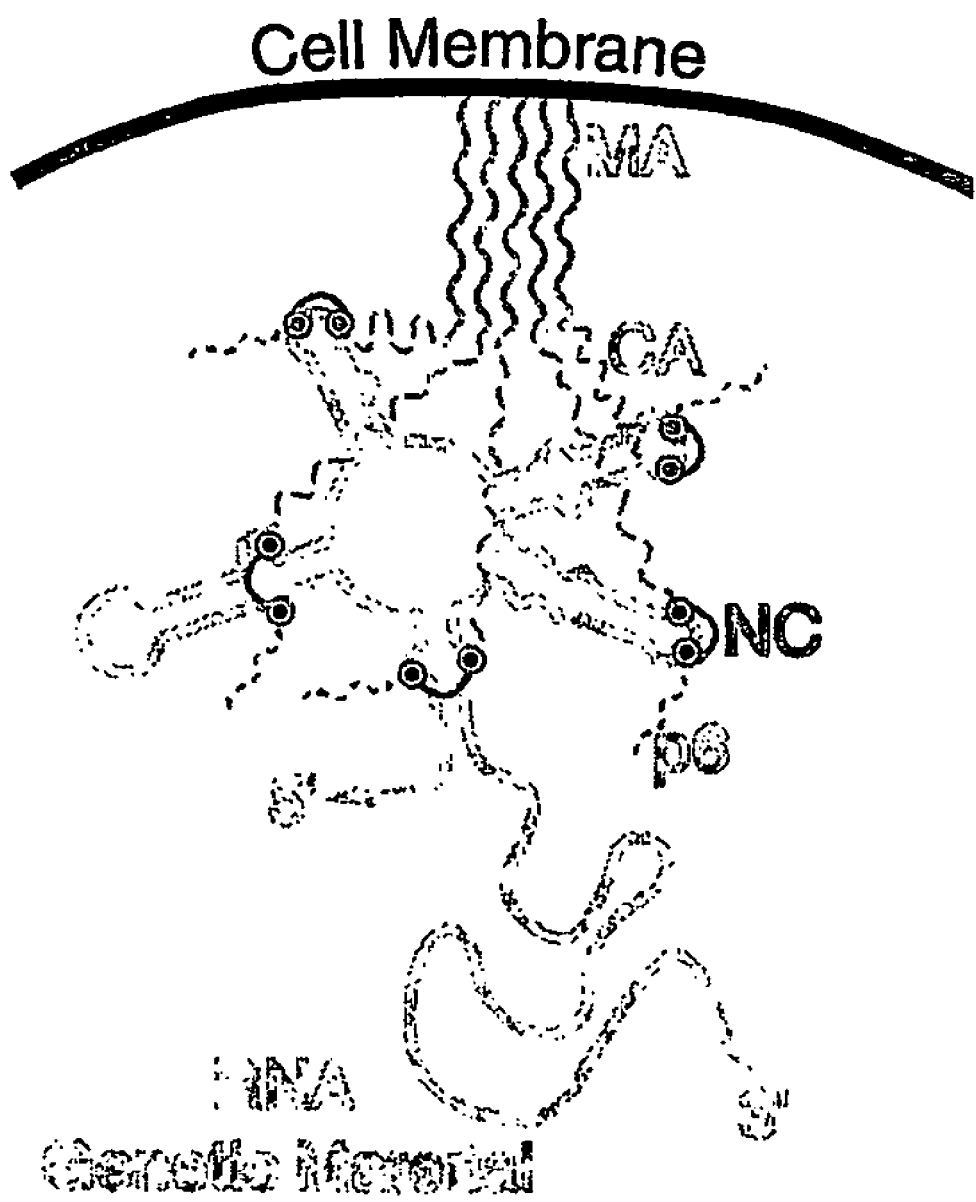

| | | | |
|---|---|---|---|
| 5,925,517 | A | 7/1999 | Tyagi et al. |
| 6,451,588 | B1 | 9/2002 | Egholm et al. |
| 6,569,630 | B1 | 5/2003 | Vivekanada et al. |
| 6,680,377 | B1 | 1/2004 | Stanton et al. |
| 2003/0087239 | A1 | 5/2003 | Stanton et al. |
| 2003/0165837 | A1 | 9/2003 | Boger |
| 2005/0064471 | A1 | 3/2005 | Griffey et al. |

FOREIGN PATENT DOCUMENTS

| | | |
|---|---|---|
| WO | WO 03/054223 | 7/2003 |
| WO | WO 2004/069850 | 8/2004 |

OTHER PUBLICATIONS

DeBaar, M. P. et al., "Detection of Human Immunodeficiency Virus Type 1 Nucleocapsid protein p7 In Vitro and In Vivo", J. Clin. Microbiol., vol. 37, pp. 63-67 (1999).*

Kim, S. J. et al., "Selection and Stabilization of the RNA Aptamers against the Human Immunodeficiency Virus Type-1 Nucleocapsid Protein", Bichem. Biophys. Res. Comm., vol. 291, pp. 925-931 (2002).*

Frauendorf, et al. "Detection of Small Organic Analytes by Fluorescing Molecular Switches," *Bioorganic & Medicinal Chemistry*, vol. 9, pp. 2521-2524, 2001.

Nutiu, et al. "Structure-Switching Signaling Aptamers: Transducing Molecular Recognition into Fluorescence Signaling," *Chem. Eur. J.*, vol. 10, pp. 1868-1876, 2004.

Yamamoto, et al. "Molecular Beacon Aptamer Fluoresces in the Presence of Tat Protein of HIV-1," *Genes to Cells*, vol. 5, pp. 389-396, 2000.

Sekella, et al. "A Biosensor for Theophylline Based on Fluorescence Detection of Ligand-Induced Hammerhead Ribozyme Cleavage," *RNA*, vol. 8, pp. 1242-1252, 2002.

International Search Report.

Soukup, et al., "Nucleic Acid Molecular Switches," *Trends in Biotechnology*, vol. 17, No. 12, pp. 469-476, 1999.

Shubsda, et al. "Affinities of Packaging Domain Loops in HIV-1 RNA for the Nucleocapsid Protein," *Biochemistry*, vol. 41, pp. 5276-5282, 2002.

Communication relating to the results of the partial international search report which issued Aug. 4, 2006.

Boiziau, et al. "DNA Aptamers Selected Against the HIV-1 trans-Activation-Responsive RNA Element Form RNA-DNA Kissing Complexes," *The Journal of Biological Chemistry*, vol. 274, No. 18, pp. 12730-12737, Apr. 30, 1999.

International Search Report dated Aug. 28, 2006.

Tyagi, et al. "Molecular Beacons: Probes that Fluoresce upon Hybridization," *Nature Biotechnology*, vol. 14, pp. 303-308, Mar. 1, 1996.

Hartig, et al. "Reporter Ribozymes for Real-time Analysis of Domain-specific Interactions in Biomolecules: HIV-1 Reverse Transcriptase and the Primer Template Complex," *Angew. Chem. Int. Ed.*, vol. 41, No. 22, pp. 4263-4266, 2002.

Jayasena, "Aptamers: An Emerging Class of Molecules that Rival Antibodies in Diagnostics," *Clinical Chemistry*, vol. 45, No. 9, pp. 1628-1650, Jan. 1, 1999.

Supplementary European Search Report dated Apr. 22, 2009.

Ben-Asouli, et al. "Recognition of 5'-Terminal TAR Structure in Human Immunodeficiency Virus-1 mRNA by Eukaryotic Translation Initiation Factor 2," *Nucleic Acids Research*, vol. 28. No. 4, pp. 1011-1018, 2000.

* cited by examiner

SWITCHABLE NUCLEIC ACIDS FOR DIAGNOSTICS, SCREENING AND MOLECULAR ELECTRONICS

RELATED APPLICATIONS

This application is the U.S. National Phase under 35 U.S.C. §371 of International Application PCT/2004/003002, filed Feb. 3, 2004, which claims priority of U.S. Provisional Application No. 60/445,090, filed Feb. 4, 2003.

BACKGROUND OF THE INVENTION

1. Field of the Invention

In one embodiment, the present invention relates to nucleic acid constructs and methods of using these constructs to rapidly screen for target molecule interactions. More particularly, an RNA/DNA chimera comprising a fluorophore-quencher pair and a nucleic acid construct is disclosed for the rapid screening of interactions between the HIV-1 nucleocapsid protein, NCp7, and a stem-loop region, SL3, of the HIV-1 RNA, or antagonists thereof; this interaction is primarily responsible for packaging specificity in HIV-1. The compositions and methods disclosed herein can be used in preferred aspects of the present invention for diagnosing disease states, distinguishing the presence of infectious or toxic agents, drug discovery and design, and molecular electronic applications.

2. Description of the Related Art

HIV-disease causes great suffering and death in the U.S., and millions are dying worldwide. Even though the number of deaths in the United States from HIV-disease has declined in recent years, the worldwide epidemic is out of control. This ever-larger number of infected people is a direct threat to everyone because HIV-1 mutates so rapidly. The larger the pool of infected individuals, the more rapidly drug-resistant strains will emerge. The reverse transcriptase makes so many errors that every single point mutation occurs daily in newly infected cells (Coffin, J. M. (1995) *Science* 267:483-9), and nearly 1% of all possible double mutations occur (Perelson, A. S. et al. (1997) *AIDS* 11 (*suppl. A*) S17-34). Combinations of drugs used in "Highly Active AntiRetroviral Therapy" (HAART) treatment regimes target different parts of the viral life cycle. In the face of such a high mutation rate, it is clear that failures in the HAART approach must occur with increasing frequency using existing drugs. Resistant strains already exist for all currently used protease and reverse transcriptase inhibitors (Pillay, D. et al. (2000) *Rev. Med. Virol.* 10:231-53), the most potent weapons in the battle against AIDS.

Even if an effective vaccine is developed to prevent new HIV-1 infections, there will still remain a need to treat millions of AIDS victims. Their long-term treatment will require new generations of drugs. Anti-nucleocapsid protein drugs, as well as agents directed at other potential HIV targets, such as anti-rev and anti-tat, could be combined with current and next generation drugs for a multi-pronged attack that would be difficult for the virus to evade. Adding these drugs to present HAART treatments may provide highly specific and potent antiretroviral treatments. Such drugs may greatly diminish the devastating effects of HIV-related disease around the world.

SUMMARY OF THE INVENTION

In one aspect, the present invention relates to a molecular switch for interacting with a ligand and generating a detectable signal. The nucleic acid switch comprises a ligand binding domain, a framework and a signaling apparatus, which is adapted to generate the signal. The signaling apparatus can be comprised of a fluorophore and a quencher located along the framework. The fluorophore and quencher have changeable positions relative to one another. The molecular switch is adapted to change from a first conformation to a second conformation upon binding of the ligand. The relative positions of the fluorophore and quencher change when the nucleic acid switches between first and second conformations, such that the signal generated by the signaling apparatus produces a detectable change. A signaling apparatus using fluorescence and fluorescence quenching, as embodied in molecular beacons (Tyagi, S. & Kramer, F. R. (1996) *Nat Biotechnol* 14:303-8), represents one among several technologies to read out the state of the switch.

In preferred modes of the molecular switch, the switch is a nucleic acid. More preferably, the nucleic acid switch comprises a double-hairpin construct. Yet more preferably, the nucleic acid switch is bistable—i.e., both first and second conformations are stable. In another embodiment, the first and second stable conformations of the switch further comprise double helical and cruciform structures, respectively.

In one mode, the ligand binding domain comprises a naturally-occurring RNA binding site or analog thereof, or a naturally-occurring DNA binding site or analog thereof. Alternatively, the ligand binding domain comprises a combinatorially-derived sequence or related fragment, which is empirically chosen to bind to the ligand.

Preferably the bistable nucleic acid switch exhibits a binding affinity for the ligand of Kd<1 µM.

In one preferred mode of the present invention, the bistable nucleic acid switch comprising a nucleic acid sequence selected from the group consisting of SEQ ID Nos. 1, 2, 3, 4 and 5.

The bistable nucleic acid switch may be designed to bind to ligands selected from the group consisting of NC, tat, and rev proteins from HIV-1. In a preferred mode, the ligand binding domain is adapted to bind NCp7. Alternatively, the ligand binding domain may be adapted to bind a ligand involved in the etiology of a viral infection which is selected from the group consisting of Hepatitis C, Congo-Crimean hemorrhagic fever, Ebola hemorrhagic fever, Herpes, human cytomegalovirus, human pappiloma virus, influenza, Marburg, Q fever, Rift valley fever, Smallpox, Venezuelan equine encephalitis, HIV-1, MMTV, HIV-2, HTLV-1, SNV, BIV, BLV, EIAV, FIV, MMPV, Mo-MLV, Mo-MSV, M-PMV, RSV, SIV, AMV.

In another variation, the ligand binding domain may be adapted to bind a ligand selected from the group consisting of TAR-tat, RRE-rev, DIS, PBS, RT, PR, IN, SU, TM, vpu, vif, vpr, nef, mos, tax, rex, sag, v-src, v-myc and precursors and protease products of the precursors, gag, gag-pol, env, src, and onc as collected in Appendix 2 of (Coffin, J. M., Hughes, S. H., Varmus, H. E. (1997) Retroviruses, Cold Spring Harbor Lab Press, Plainview, N.Y.).

In another variation, the ligand binding domain may be adapted to bind a ligand derived from an organism selected from the group consisting of bacteria, fungi, insects, and pathogens and pests to humans, animals, and plants. Further, the ligand binding domain may be adapted to bind a toxin or other factor derived from bacteria and other microorganisms selected from the group consisting of *B. anthracis, Burkholderia pseudomallei*, Botulinum, Brucellosis, *Candida albicans, Cholera, Clostridium perfringins*, Kinetoplasts, Malaria, Mycobacteria, Plague, *Pneumocystis*, Schistosomal parasites, *Cryptosporidium, Giardia*, and other environmental contaminants of public and private water supplies, Ricin, Saxitoxin, Shiga Toxin from certain strains of *E. coli*, *Staphylococcus* (including enterotoxin B), Trichothecene mycotoxins, Tularemia, and agents causing Toxoplasmosis, as well as contaminants of food and beverages that may be deleterious to human or animal health.

Figure 5:
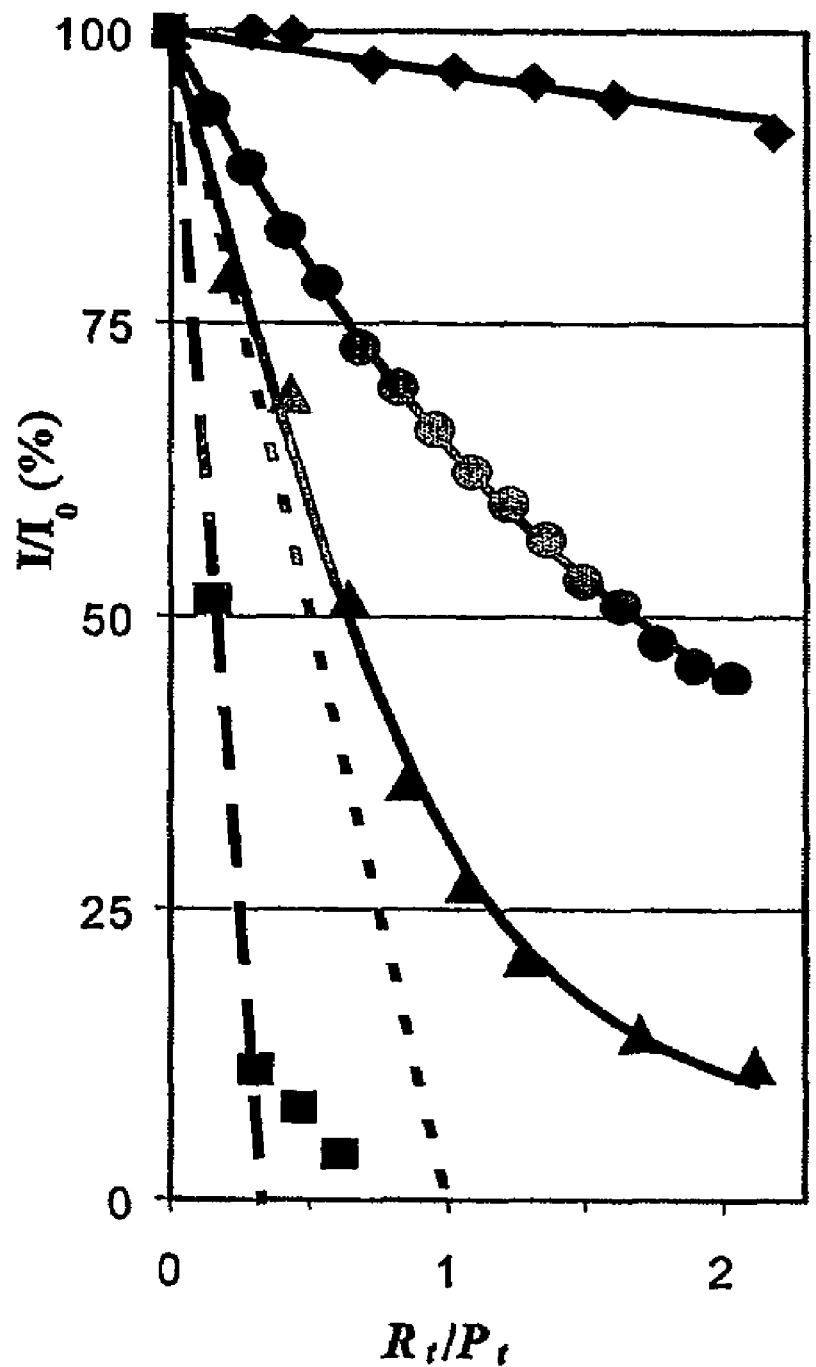

In another embodiment, the ligand binding domain may be adapted to bind a small-molecule target selected from the group consisting of nerve gas agents and chemical poisons, as well as contaminants of public and private water supplies, of food and beverages, and of indoor air that may be deleterious to human or animal health.

In another preferred embodiment of the present invention, a diagnostic method is disclosed for detecting the presence of a ligand molecule in a sample. The diagnostic method comprises the steps of: (1) providing a bistable molecular switch with a ligand binding domain, a molecular framework and a signaling pair adapted to generate a fluorescent signal. The signaling pair comprises a fluorophore and a quencher which have changeable positions relative to one another. The molecular switch is adapted to vary between first and second stable conformations upon binding of the ligand, wherein the relative positions of the fluorophore and quencher change when the molecular switch varies between first and second stable conformations, such that the fluorescent signal changes; (2) contacting the molecular switch with the sample; and (3) monitoring changes in the fluorescent signal.

In a preferred variation to the diagnostic method, the molecular switch comprises a chimeric DNA-RNA molecule. The molecular framework may comprise DNA, and the ligand binding domain may comprise RNA. This does not exclude the possibility of the ligand binding domain or molecular framework being composed of either RNA or DNA, nor does it exclude the possibility of one or more monomers in the chain being composed of a modified nucleotide. In one embodiment, the ligand binding domain may comprise a combinatorially-derived sequence which has been empirically chosen to bind said ligand. Preferably, the combinatorially-derived sequence has an affinity for the ligand of at least Kd <1 μM.

The diagnostic method may be adapted to detect ligands selected from an infectious organism or toxic agent. In one mode, the diagnostic method may be adapted for use in a field kit for real-time detection of infectious organisms or toxic agents.

In another preferred embodiment of the present invention, an assay method is disclosed for discovering a chemical entity that interferes with a natural RNA or DNA for binding of a ligand. The assay method comprises the steps of: (1) providing a bistable molecular switch, comprising an analog of the RNA or DNA, wherein the analog comprises the ligand binding domain. The bistable molecular switch further comprises a molecular framework and a signaling pair adapted to generate a fluorescent signal. The signaling pair preferably comprises a fluorophore and a quencher which have changeable positions relative to one another. The molecular switch is adapted to vary between first and second stable conformations upon binding of the ligand, wherein the relative positions of the fluorophore and quencher change when the molecular switch varies between first and second stable conformations, such that the fluorescent signal changes; (2) contacting the molecular switch with the ligand in the absence of the chemical entity, and monitoring the fluorescent signal; (3) contacting the molecular switch with the ligand in the presence of the chemical entity, and monitoring the fluorescent signal; and (4) comparing the fluorescent signals generated in the presence and absence of the chemical entity to determine whether the chemical entity altered the amount of ligand bound to the ligand binding domain.

The molecular switch used in the assay method preferably comprises a chimeric DNA-RNA molecule, wherein the ligand binding domain comprises RNA, the molecular framework comprises DNA, and the ligand is a viral protein. This does not exclude the possibility of the ligand binding domain or molecular framework being composed of either RNA or DNA, nor does it exclude the possibility of one or more monomers in the chain being composed of a modified nucleotide.

In one variation to the assay method, the step of contacting the molecular switch with the ligand in the presence of the chemical entity, further comprises allowing the molecular switch and the ligand to equilibrate prior to adding the chemical entity. Preferably, the molecular switch is adapted to generate a null fluorescent signal upon equilibration with the ligand.

In another variation to the assay method, the ligand binding domain may comprise a combinatorially-derived sequence which has been empirically chosen to bind said ligand.

In another preferred embodiment of the present invention, a bistable molecular switch is disclosed for use in molecular electronics. The molecular switch comprises a ligand binding domain comprising a combinatorially-derived sequence empirically chosen to bind a photosensitive ligand adapted to alter between first and second energy states upon application of triggering photons, wherein the binding affinity of the ligand binding domain for the ligand is greater in one energy state compared to the other energy state. The molecular switch also comprises a molecular framework encompassing the ligand binding domain. The framework is adapted to switch from a first stable conformation to a second stable conformation upon binding of the photosensitive ligand by the ligand binding domain. Finally, the molecular switch also comprises a signaling pair adapted to generate a detectable signal, comprising a signaling element and a quencher which have changeable positions relative to one another and are located along the molecular framework, wherein the relative positions of the signaling element and quencher change when the molecular framework switches between first and second stable conformations, such that the detectable signal varies upon application of the triggering photons.

BRIEF DESCRIPTION OF THE DRAWINGS

FIG. 1 is a schematic view of packaging in HIV-1 as a new virus particle assembles at the membrane of an infected cell. Each virus has two identical RNA strands, about 1500 gag and gag-pro-pol precursor proteins, and several other proteins and cellular components. As the virus matures, the precursors are processed into separate proteins, including NCp7. Within the precursor, the NC domains recognize sets of two loop G-residues ($G_2$ loci) in the RNA 5'leader.

FIG. 2 shows the HIV-1 NCp7 protein. Residues carrying a charge at neutral pH are shown in outlined letters (positive=capitals, negative=lower-case); $Zn_2$.NCp7(1-55) carries a +9 charge at neutral pH.

FIG. 3 is the hypothetical secondary structure of the HIV-1 RNA domain near the 5'-major splice donor (SD) (Pappalardo, L. et al. (1998) *J. Mol. Biol.* 282:801-818). Several known and potential $G_2$-loci are noted.

FIG. 4 is a detailed view of part of the packaging signal interaction, showing the SL3-NCp7 complex (DeGuzman, R. et al. (1998) *Science* 279:384-388). It can be seen that W37 of the protein stacks on G318.

FIG. 5 illustrates quenching W37 in NCp7 by four HIV-RNA molecules. ◆ SL3-UUCG, ● SL4, ▲ SL3, ■ 154mer full domain; solid lines represent calculated fits for 1:1 complexes (see text). Short dashed line: ideal $R_1P_1$ complex, long dashes: ideal $R_1P_3$ complex. $R_t$ and $P_t$ are the total concentrations of RNA and NCp7, respectively.

Figure 6:
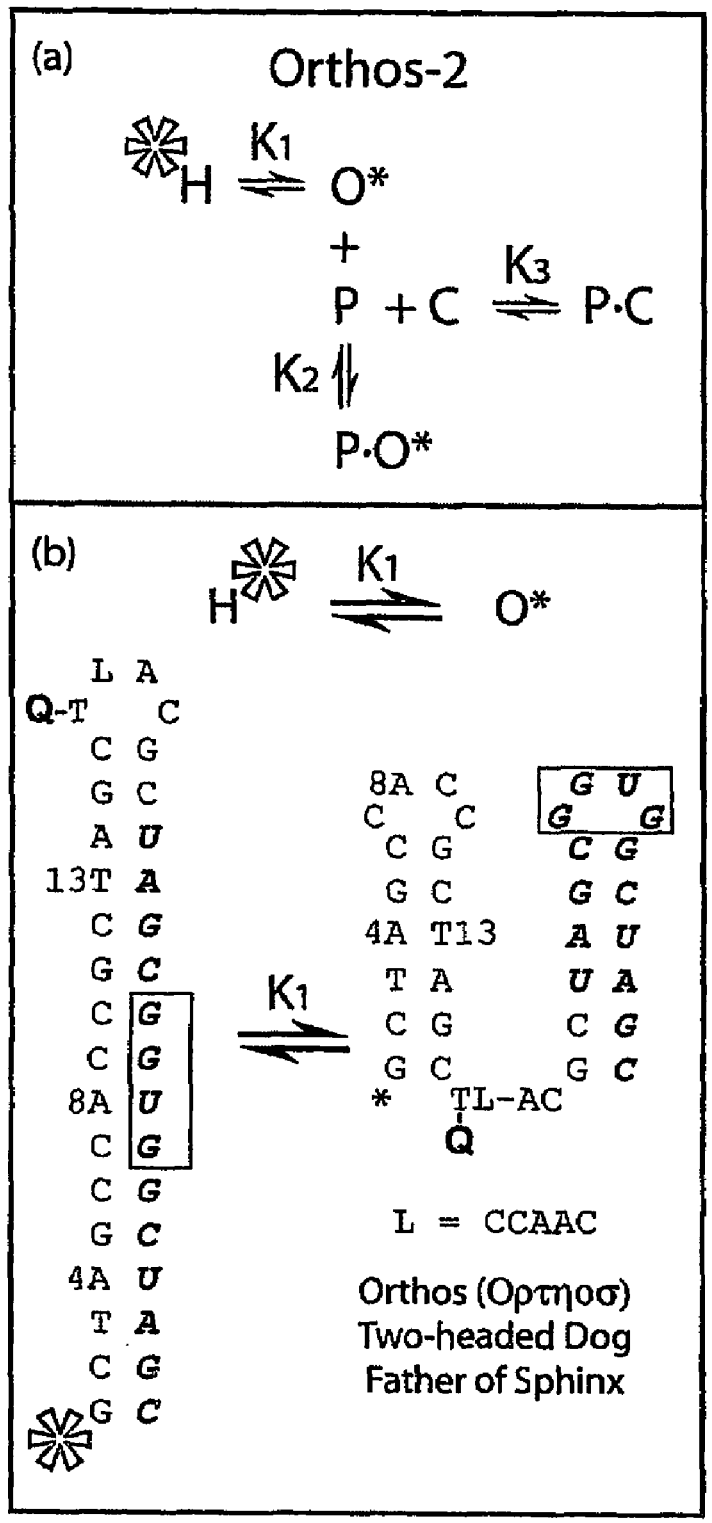

FIG. 6 shows the equilibria for the SL3-NCp7 assay using a chimeric fluorescent switch in accordance with one embodiment of the present invention. (a) Fluorescence assay used to detect competitors of SL3-NCp7 complex formation. (b) Chimeric switches have two stable states: an extended hairpin, H, at left, and double hairpin, O, at right. Fluorophore=*, quencher=Q, protein=P, competitor=C. RNA strands are denoted in dark italics, DNA in lighter font.

Figure 7:
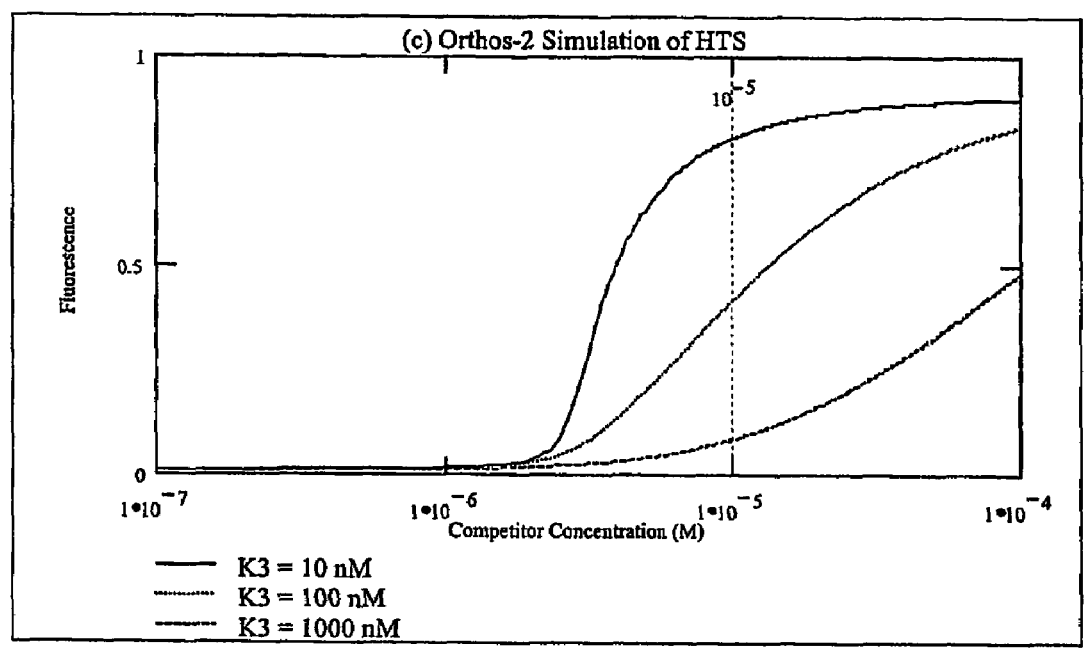

FIG. 7 shows competitor thresholds for the fluorescent RNA/DNA chimera illustrated in FIG. 6(b), $O_t$=0.3 µM, $P_t$=3 µM, $K_1$=0.1 nM, $K_2$=3 nM. Values of $K_3$ are indicated below the graph.

Figure 8:
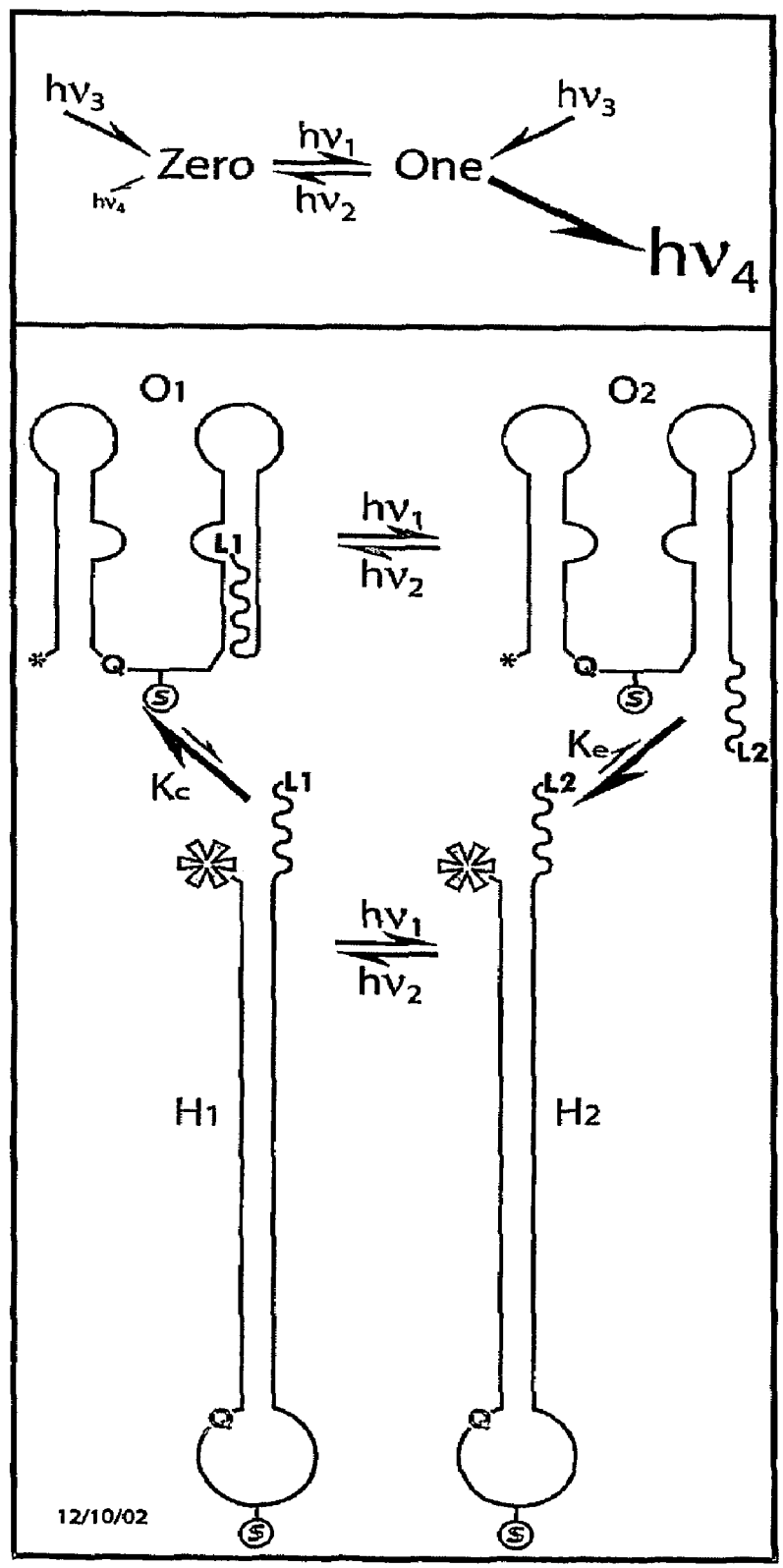

FIG. 8 shows a basic module for molecular electronic applications. Top: A preferred digital system has states "Zero" and "One", which are switched by application of light at frequencies $v_1$ (Write) and $v_2$ (erase); the state of the system is interrogated at $v_3$ (Read) and detected at $v_4$. Bottom: Schematic of switchable nucleic acid constructs to support the preferred embodiment.

DETAILED DESCRIPTION OF THE PREFERRED EMBODIMENT

All of the references cited in this application are expressly incorporated herein by reference thereto. Any technical terms and abbreviations, not explicitly defined below, are to be construed in accordance with their ordinary meaning as understood by one of skill in the art of molecular biology. For example, A, C, G, T and U are standard one-letter symbols for the nucleotide bases, adenine, cytosine, guanine, thymine and uracil, respectively. The following specific abbreviations are used in this application:

A refers to a bistable RNA and/or DNA construct (except where A is used to designate adenine in a nucleotide sequence)

combinatorially-derived sequence refers to a nucleic acid molecule adapted to bind to a specific molecular target, such as a protein or metabolite C refers to any molecules that compete with or otherwise interfere with binding of L to natural RNA or DNA analogs of A L refers to a ligand molecule HIV-1 refers to the human immunodeficiency virus 1

NC is nucleocapsid

NCp7 is the 55 amino acid nucleocapsid protein of HIV-1

SL1, SL2, SL3 and SL4 refer to consecutive short stem-loop segments of RNA from the 5'-leader region of HIV-1

S/N is signal to noise ratio

W37 is tryptophan residue 37 of NCp7

This invention relates to the design and application of bistable RNA and/or DNA constructs (A) that are switchable between two thermodynamically stable states; the constructs may also be composed partially or entirely of mimetics of nucleic acids. One of the stable states includes a site for binding a target protein, nucleic acid, saccharide, small molecule, or supramolecular assembly. This binding site is sequestered in the second stable state. The detailed nature of the construct depends on the target. An example is provided for discovery of a natural RNA-protein target that can be included in a double-hairpin construct. Other targets may bind natural RNA or DNA sequences, or may be introduced via in vitro experiments to choose "combinatorially-derived sequence" molecules. The technology disclosed herein enables one skilled in nucleic acid chemistry and biophysical chemistry to create a suitable bistable construct and fine-tune the relative stability of the two forms.

Areas of Contemplated Use (1) Diagnostic tests for the presence of a protein, nucleic acid, supramolecular structure, whole or inactivated organism, or other ligand molecule (L) that binds preferentially to one of the two stable states of A. This stable state contains an analog of a naturally occurring RNA or DNA binding site for L (ligand binding domain).

(2) The discovery of chemical entities (C) that interfere with binding of L to natural RNA or DNA analogs of A. One application involves C molecules that are leads for therapeutic agents against a disease state for which A-L interactions are necessary, e.g., interactions between SL3 of HIV-1 RNA and NCp7.

(3) Applications similar to (1), wherein the ligand binding domain of A comprises a combinatorially-derived sequence that is empirically chosen to bind tightly and specifically to L. Embodiments include field kits for real-time detection of infectious organisms or toxic agents.

(4) Applications similar to (2), wherein the ligand binding domain of A comprises a combinatorially-derived sequence that is empirically chosen to bind tightly and specifically to L. Embodiments include the discovery of chemical agents, C, for the remediation of effects due to infectious or toxic agents, L.

(5) Molecular electronic applications where the state change in A occurs in response to a triggering impulse, which may be a light pulse that alters the state of a photosensitive ligand, L1, to L2. In these applications, the ligand binding domain of A may contain a natural RNA or DNA binding site for L1 or L2, or a combinatorially-derived sequence sequence empirically chosen to bind tightly and specifically to either L1 or L2. The shape and properties of A will depend upon whether the combinatorially-derived sequence-binding pocket is occupied. Here, the construct may include a fluorophore quencher pair or other signal generating elements.

The invention relies on a conformationally bistable construction for A that is switched from one state (A1) to the other (A2) upon binding L. In the A2-L complex, the molecular conformation, A2, differs from that which predominates in the unbound state, A1. The state change may be detected by a change in fluorescence, because the fluorescent properties of A1 and A2 are designed to be very different. The fraction of A that is present as the A2-L complex is controlled by several thermodynamic factors, including (i) the relative affinity of L for A1 and A2, (ii) the A1/A2 equilibrium, and (iii) the input concentrations of the species. Some applications will include competitors, C, for the A2-L interaction, in which case the affinities of C for L, A1, and A2 are also relevant.

An embodiment of item (2), above, is used to illustrate the invention, where a bistable RNA/DNA chimera including a fluorophore-quencher pair is disclosed for the rapid screening of agents to disrupt the SL3-NCp7 interaction in HIV-1. That embodiment is described in detail below. In that description, H, O, and P replace the general nomenclature, A1, A2, L, respectively.

The general operation of the invention requires the construction of an RNA and/or DNA (or other natural or nucleotide mimetic analogs) molecule that is switchable between two thermodynamically stable states. Illustrations and working examples are disclosed for double-hairpin constructs and cruciform structures.

HIV-1 has fifteen proteins and two identical RNA strands. Each of these is a potential target for drug interdiction. More details are given in several reviews and books (Frankel, A. D. and Young, J. A. T (1998) Ann. Rev. Biochem. 67:1-25; Coffin, J. M. et al. (1997) Retroviruses, Cold Spring Harbor Lab. Press, Plainview, N.Y.; Gallo, R. C., & Jay, G., eds. (1991) *The Human Retroviruses*, Academic Press, New York). Drugs currently in use target the viral reverse tranScriptase (RT) and protease (PR). There are also efforts to develop integrase (IN) and fusion inhibitors, but these may not be clinically useful in the inmediate future. Several other HIV targets have been suggested. These include the nucleocapsid protein, as well as tat and rev (Frankel, A. D., and Young, J. A. T (1998) *Ann. Rev. Biochem.* 67:1-25).

For HIV to reproduce, genomic RNA and viral proteins must form a packaging complex," illustrated in FIG. 1. The 5'-leader region of the RNA contains sequences that allow only infectious RNA to be packaged into new virus particles, selected from the millions of other RNA molecules in a cell.

The NC domain or mature NCp7 has roles in packaging the RNA (Wills, J. W., & Craven, R. C. (1991) *AIDS* 5:639-654; Oertle, S. and Spahr, P. (1990) *J. Virol.* 64:5757-5763; Damgaard, C. K. et al. (1998) *Nucleic Acids Res.* 26:3667-76; DeGuzman, R. et al. (1998) *Science* 279:384-388), "chaperoning" functions (Williams, M. C. et al. (2001) *Proc Natl Acad Sci U S A* 8:8), in refolding the RNA dimer in the virion (Fu, W. and Rein, A. (1994) *J. Virol.* 68:5013-5018), and annealing the primer tRNA onto the genomic RNA for reverse transcription (Prats, A. C. et al. (1988) *EMBO J.* 7:1777-1783). It also interacts with viral proteins including reverse transcriptase (Druillennec, S. et al. (1999) *J. Biol. Chem.* 274:11283-8; Lener, D. et al. (1998) *J. Biol. Chem.* 273:33781-6), and the accessory protein, Vpr, to play a role in stable integration of the proviral DNA in the chromosomes of infected cells (de Rocquigny, H. et al. (2000) *Eur. J. Biochem.* 267:3654-60). Thus, drugs that target the nucleocapsid protein and/or its interactions with other HIV-1 molecules have the potential to interfere with critical functions at many stages of the viral life cycle (Darlix, J. L. et al. (2000) *Adv. Pharmacol.* 48:345-72; Berthoux L. et al. (1999) *J. Virol* 73:10000-9).

The NC, tat, and rev proteins all interact with RNA in regions that can be created with the fluorescent RNA/DNA chimeras in accordance with preferred embodiments of the present invention, as described below in greater detail. Thus, those of ordinary skill in the art will appreciate that the compositions and methods used to screen anti-NC candidates disclosed herein can be readily adapted for these other HIV-1 targets as well.

Anti-NC Strategies

A goal of targeting an enzyme with an equilibrium-binding agent is to decrease the enzyme's turnover rate. Small changes in the binding free energy of competitors may be amplified by exponential decreases in turnover. Thus, drugs having micromolar or even millimolar affinities may be sufficiently effective as long as Absorption, Distribution, Metabolism, Elimination, Toxicity ("ADME/Tox") properties are favorable. This is the fundamental advantage in targeting RT, PR, or IN over viral substances that exert their influence by mass action. On the other hand, this amplifier effect confers a strong survival advantage on mutants resistant to a drug. In a short time, a mutant strain can dominate an infection.

The mature NCp7 protein presumably turns over in its chaperoning activity. Thus, it is possible there will be an amplifier effect similar to that for equilibrium binding drugs to inhibit RT, PR, or IN. The packaging function of NC, however, seems to be dominated by mass action—2000 gag precursor proteins are available to recognize the packaging domain RNA for each virus. An answer to mass action is tighter binding. Thus, the preferred target drugs will exhibit high affinity binding to the HIV-1 RNA.

A possible way to skirt problems due to low affinity or a mass-action function is for a drug to covalently inactivate the target. There have been attempts to adapt sulfur-reactive compounds to attack cysteine side chains in the zinc fingers (Rice W G et al. (1993) *Nature* 361:473-5; Rice W G et al. (1995) *Science* 270:1194-7; Chertova E N et al. (1998) *Biochemistry* 37:17890-7; Huang M et al. (1998) *J Med Chem.* 41:1371-81; Guo J et al. (2002) *J Virol.* 76:4370-8; Yovandich J L et al. (2001) *J Virol.* 75:115-24; Berthoux, L et al. (1999) *J Virol* 73:10000-9). Cys49, in the C-terminal finger (FIG. 2), reacts fastest with N-ethylnaleimide (NEM) in vitro (Chertova E N et al. (1998) *Biochemistry* 37:17890-7). A cascade of reactions then ejects $Zn^{2+}$ from both fingers. The reaction with NEM is slow even at relatively high concentrations (~8 mM NCp7, 50 mM NEM; $t_{1/2} \cong 30$ min for forming the C49 adduct).

Other "zinc-ejecting" alkylating agents have been tested (Rice W G et al. (1993) *Nature* 361:473-5; Rice W G et al. (1995) *Science* 270:1194-7; Chertova E N et al. (1998) *Biochemistry* 37:17890-7; Huang M et al. (1998) *J Med Chem.* 41:1371-81; Guo J et al. (2002) *J Virol.* 76:4370-8; Yovandich J L et al. (2001) *J Virol.* 75:115-24; Berthoux, L et al. (1999) *J Virol* 73:10000-9). However, cysteines are common, as are zinc-chelating proteins. Thus, zinc ejection seems to violate the principle that one should attack HIV at processes that are specific to the virus.

In an attempt to counter this concern, some reagents were tested with zinc-containing transcription factors. The experimenters suggested that the reagents were selective for reaction with NC, while the cysteines chelating zinc in the fingers of the transcription factors were not alkylated. However, examination of the protocol (Huang M et al. (1998) *J Med Chem.* 41:1371-81) shows that the latter reaction was conducted in the presence of the DNA substrate for the cellular protein. Alkylation of Cys49 can be stopped almost completely by preincubating NCp7 with $d(GT)_n$ oligomers in 2-fold excess (Chertova E N et al. (1998) *Biochemistry* 37:17890-7); these bind much more weakly than the natural RNA substrates for NC (see EXAMPLES). Selectivity then remains an open question. It is likely that both NC and cellular transcription factors are present mostly as RNA or DNA-bound forms.

Others have experimented with short single-stranded DNA molecules (Vuilleumier, C et al. (1999) *Biochemistry* 38:16816-25; Mely, Y et al. (1994) *Biochemistry* 33:12085-91; Maki, A. H. et al. (2001) *Biochemistry* 40:1403-1412; Fisher, R. J. et al. (1998) *J Virol* 72:1902-9), or DNA and NC mimetics (Druillennec S et al. (1999) *Bioorg Med Chem Lett.* 9:627-32; Druillennec S et al. (1999) *Proc Natl Acad Sci USA.* 96:4886-91). The $K_d$ values are probably in the millimolar range at best, although this is difficult to confirm.

In work on deoxy dinucleotides where the phosphodiester was replaced by a methylene carboxamide linker (Druillennec S et al. (1999) *Bioorg Med Chem Lett.* 9:627-32), $K_d$ values for NC binding were estimated at 6 μM for TG, 100 μM for GT, and >1000 μM for TT. Protein binding for the dinucleotides is considerably weaker than for SL3 or SL2 RNA, but it is encouraging that uncharged molecules with MW ~500 exhibit both affinity and sequence specificity. The other conclusions are that the TG molecule: (i) penetrates cells in an HIV-1 infected cell line, (ii) inhibits RT activity by 20% at a concentration of 10 μM, and (iii) appears to snap NC into the same binding conformation given that shifts in the NMR spectrum of NC are similar to those induced by longer nucleic acids.

A cyclic peptide that competes with NC for in vitro recognition of its RNA, DNA and protein targets may function as a mimic for NC (Druillennec, S et al. (1999) *Proc Natl Acad Sci USA* 96:4886-91). This hexapeptide, c(F-C-dW-R-C-K), has strong structural similarities in the locations of W, F, and basic side chains in NCp7. It also exhibits In vivo effects that suggest impairment of proviral DNA synthesis, perhaps by direct interaction with RT or by interfering with annealing the tRNA primer to genomic RNA.

There is also some enthusiasm for competitive inhibitors based on RNA aptamers that have been created with nanomolar affinities for NCp7 (Lochrie, M. A. et al. (1997) *Nucleic Acids Res* 25:2902-10; Berglund, J. A. et al. (1997) *Nucleic Acids Res* 25:1042-9; Allen, P. et al. (1996) *Virology* 225:306-15). Most of the binding studies were conducted at low salt and the stoichiometry was not clearly established. Therefore, some of these molecules are considered as possible candidates herein. However, unmodified DNA and RNA molecules may not readily pass the cell membrane and survive long enough in a cell to disrupt the target NC-RNA interaction.

The present screening methods are deemed applicable for the high-throughput assay of low-molecular weight lead compounds. Generally, low-MW drugs are more permeable to cell membranes than macromolecules, are accessible by organic synthesis, and pharmaceutical companies are experienced in formulating similar compounds for oral dosage. Libraries of thousands of "drug-like" compounds are now available for high throughput screening. They possess diverse molecular scaffolds to locate lead compounds, which can be modified by combinatorial and rational design to optimize their NC affinity, and ADME/Tox properties.

The compounds and methods disclosed with respect to the NC-RNA system should be directly applicable for developing and testing useful low-MW compounds. Indeed, the work in measuring affinities, in structure determination by NMR, and stabilizing NCp7 against denaturation, disclosed herein, can be applied in a vigorous program of anti-nucleocapsid drug discovery and design.

Structural Biology of Packaging

Figure 3:
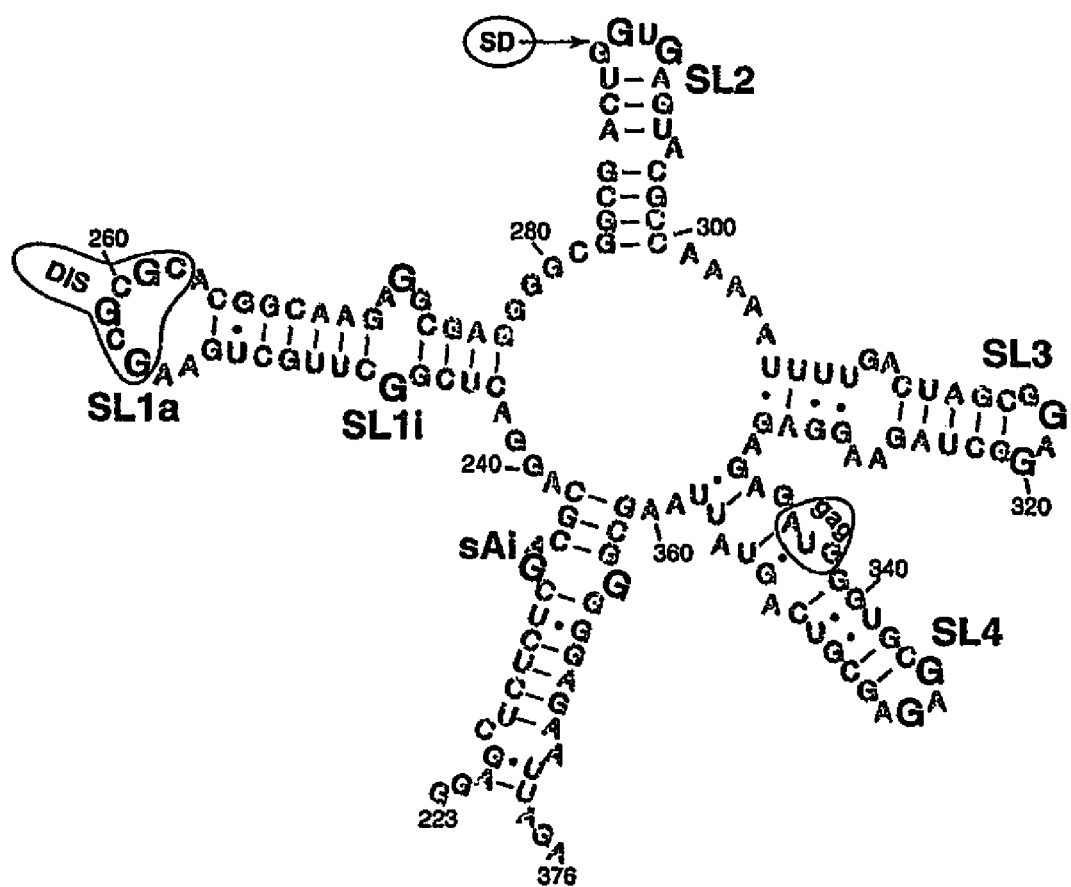

FIG. 3 shows secondary folding of the major packaging domain of HIV-1 RNA. Several elements for controlling the viral life cycle are contained within this ~150 nucleotide sequence. (1) A metastable RNA dimer forms around the dimer initiation sequence (DIS) (Muriaux, D. et al. (1996) *Biochemistry* 35:5075-82; Muriaux, D. et al. (1996) *J Biol Chem* 271:33686-92; Clever, J. L. et al. (1996) *J. Virol.* 70:5902-8; Laughrea, M. et al. (2001) *Virology* 281:109-116) in SL1, which then matures in the virion to a more stable form condensed with NCp7 (Fu, W. & Rein, A. (1994) *J. Virol.* 68:5013-5018). The mature virus has about one NCp7 per 10-12 nucleotides. (2) The 5'-major splice donor (SD) in SL2 is a primary RNA processing site. Since spliced mRNA is not packaged, it is likely that packaging determinants reside in the sequence or folded structure of the region near SD. (3) A determinant of packaging is SL3, in which two nearby guanine residues ($G_2$-loci) appear to be involved in specificity; $G_2$-loci in other stem-loops are also involved. The following paragraphs give a more complete description of the background to packaging. (4) The coding region for the gag genes begins in SL4.

Figure 2:
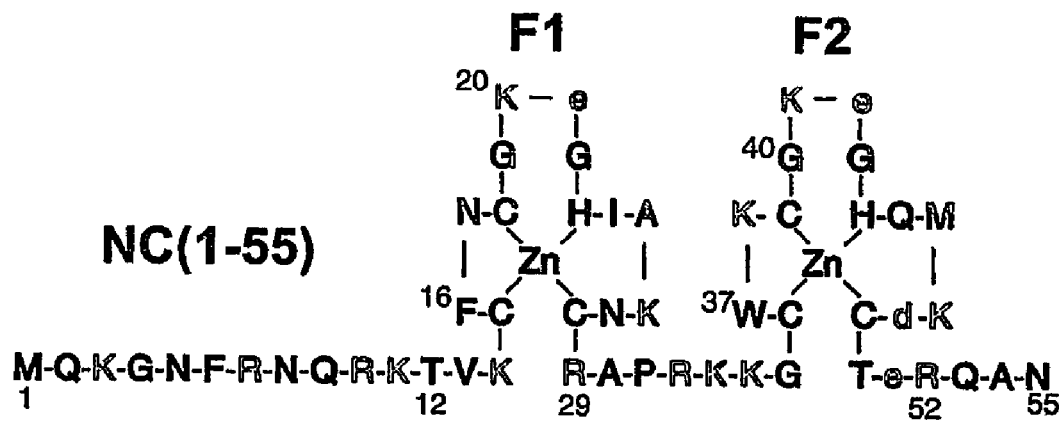

Many details of packaging in retroviruses have come into focus (Coffin, J. M. et al. (1997) *Retroviruses*, Cold Spring Harbor Lab. Press, Plainview, N.Y.; Gallo, R. C., & Jay, G., eds. (1991) *The Human Retroviruses*, Academic Press, New York; Clever, J. L. et al. (1999) *J Virol*. 73:101-9; Clever, J. L. & Parslow, T. G. (1997) *J Virol*. 71:3407-14; McBride, M. S. & Panganiban, A. T. (1996) *J Virol*. 70:2963-73; McBride, M. S. et al. (1997) *J Virol*. 71:4544-54; Clever, J. et al. (1995) *J Virol* 69:2101-9). In HIV-1 about 1500-2000 polyprotein precursors (pr-gag, and pr-gag-pol) assemble at the inner membrane of the forming virion (Vogt, V. M. & Simon, M. N. (1999) *J Virol* 73:7050-5) rather than just the few illustrated in FIG. 1. Each of these proteins contains a nucleocapsid domain that is required for packaging to occur. The 55 kD gag precursor polyprotein is later processed by the viral protease to "structural" proteins, including NCp7 (Linial, M., & Miller, A. D. (1990) *Curr. Top. Microbiol. Immunol*. 157:125-152; Gelderblom, H. R. (1991) *AIDS* 5:617-638). NC-domains within gag precursors bind to the RNA with several RNA-NC interactions responsible for full discrimination of genomic from non-genomic RNA (Clever, J. L. et al. (1999) *J Virol*. 73:101-9; Clever, J. L. & Parslow, T. G. (1997) *J Virol*. 71:3407-14; McBride, M. S. & Panganiban, A. T. (1996) *J Virol*. 70:2963-73; McBride, M. S. et al. (1997) *J Virol*. 71:4544-54; Clever, J. et al. (1995) *J Virol* 69:2101-9). The NC-domains interact via a conserved zinc finger motif (FIG. 2). Mutants of the fingers that render them incompetent for zinc binding destroy the capacity to recognize and package genomic RNA (Aldovini, A. & Young, R. A. (1990) *J Virol* 64:1920-6; Gorelick, R. J. et al. (1988) *Proc Natl Acad Sci USA* 85:8420-4; Dupraz, P. et al. (1990) *J Virol* 64:4978-87). It is thought that interactions with the two fingers in NCp7 are the same as in the precursor.

Most HIV-1 packaging specificity occurs with sequences encompassed by the nucleotides shown in FIG. 3 (Pappalardo, L. et al. (1998) in *Structure, Motion, Interaction and Expression of Biological Macromolecules*, pp. 125-135 (R. H. Sarma & M. H. Sarma, eds.); Shubsda, M. F. et al. (2002) *Biochemistry* 41:5276-82). There have also been measurements of the association constants of various RNA fragments with the 15 kDa NCp7 precursor protein (Clever, J. et al. (1995) *J Virol* 69:2101-9), and GST-NC fusion proteins (McBride, M. S. & Panganiban, A. T. (1996) J Virol. 70:2963-73) indicating that all four hairpins are involved with NC-domain interactions. Each loop is a favorable candidate for interaction with the NCp7 zinc-finger domain, with 2 or 3 G residues in single-stranded loops; G may be a requirement for interaction with the finger in the native RNA sequence (South, T. L. & Summers, M. F. (1993) *Protein Sci* 2:3-19; Summers, M. F. et al. (1992) *Protein Sci,* 1:563-574; Delahunty, M. D. et al. (1992) *Biochemistry* 31:6461-6469). Removal of SL3 reduces packaging efficiency by ~90%, but does not completely eliminate packaging (Clever, J. L. & Parslow, T. G. (1997) *J Virol*. 71:3407-14). This suggests that RNA-NC domain interactions may occur at several sites to provide full specificity.

Figure 4:
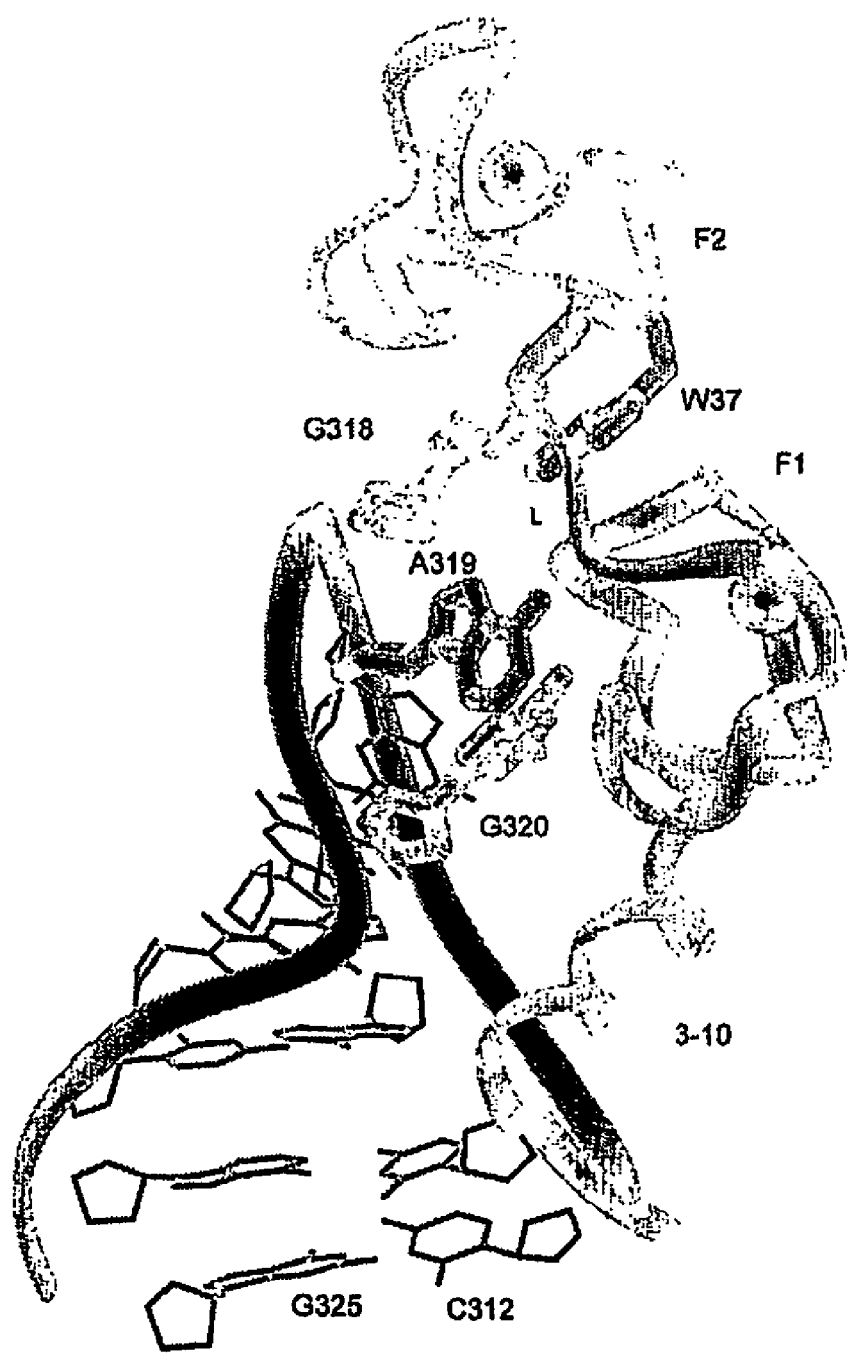

A high-resolution view of a packaging signal complex is illustrated in FIG. 4 (DeGuzman, R. et al. (1998) *Science* 279:384-388; Pappalardo, L. et al. (1998) *J. Mol. Biol*. 282: 801-818). FIG. 4 shows the complex between a 20mer SL3 construct and the 55mer NCp7. No NMR or x-ray structures for complete retroviral packaging signals have been reported, although there are several other structures for substantial subsets (Amarasinghe, G. K. et al. (2000) *J. Mol. Biol*. 299: 145-156; Amarasinghe, G. K. et al. (2000) *J. Mol. Biol*. 301: 491-511; Kerwood, D. J. et al. (2001) *Biochemistry* 40:14518-29; Mujeeb, A. et al. (1998) *Nat Struct Biol* 5:432-436; Takahashi, K. I. et al. (2000) *RNA* 6:96-102; Theilleux-Delalande, V. et al. (2000) *Eur J Biochem* 267:2711-2719;

Ennifar E et al. (2001) *Nat Struct Biol.* 8:1064-8; Zeffman, A. et al (2000) *J. Mol Biol.* 297:877-93; Morellet, N. et al. (1998) *J. Mol. Biol.* 283:419-34). There is a high degree of similarity of the interactions between NCp7 and nucleic acid in these complexes. Thus it is likely that the development and testing of anti-nucleocapsid drugs can be guided by molecular modeling based on the conserved structure.

FIG. 3 shows that splicing would destroy this secondary structure (SD is at 289-290), removing essential portions of SL2 and sA as well as all of SL3 and SL4. That provides a natural explanation for the selection of unspliced RNA for packaging. We have examined about 500 sequences in Genbank containing SL3, and found (Lin, Y. (2002) Ph.D. Thesis, Syracuse University; "Database and Algorithmic Applications in Nucleic Acid Sequence, Structure and NMR Frequencies, and in Efficient Chemical Depiction."; which is incorporated herein in its entirety by reference) that only the first and third base in the GGAG tetraloop of SL3 vary more than twice (about the rate of sequencing errors). The $G_2$-locus at 318 and 320, which is involved in the specific complex of FIG. 4, may be required for a functioning virus. G317A mutants do occur rarely, but it is predicted that A317 will stack on the stem in the same fashion as G317. Further, there are very few non-conservative variations in the NC domain. Thus, targeting the NC-SL3 interaction for drug interdiction may hold special promise in the inability of the virus to escape anti-NC drugs by mutation.

EXAMPLES

Affinities of RNA Loops for NCp7

In spite of progress in defining the packaging signal, we have characterized the stoichiometry and annuity of NC proteins for the RNA stem-loops only recently (Shubsda, M. F. et al. (2002) *Biochemistry* 41:5276-82). Part of the problem was that most early studies neglected the salt dependence of the interaction between the highly charged components (NCp7 has a charge of +9 at neutral pH, and RNA has one negative charge per phosphate). Using an ionic strength of 0.2 M reduced non-specific binding and led to full quenching of Trp-37 fluorescence, a 1:1 stoichiometry for each of the component stem-loops in the major packaging domain (Shubsda, M. F. et al. (2002) *Biochemistry* 41:5276-82; FIG. 3), and gave results consistent with NMR-based structures of SL3 and SL2 complexes (DeGuzman, R. et al. (1998) *Science* 279:384-388; Amarasinghe, G. K. et al. (2000) *J. Mol. Biol.* 299:145-156; Amarasinghe, G. K. et al. (2000) *J. Mol. Biol.* 301:491-511). We found that non-specific interactions contributed heavily to the binding at low ionic strength where most previous studies had been done (0.2 M NaCl is near physiological conditions; in blood the ionic strength is ~0.18 M ignoring contributions of charged macromolecules; Kratz, A. & Lewandrowski, K. (1998) *New Eng. J. Med.* 339:1063-1072).

We found that the $G_2$-loci noted in FIG. 3 are indeed sites for interaction with NCp7. They form complexes that have dissociation constants, $K_d$=20-300 nM at 0.2 M NaCl (Shubsda, M. F. et al. (2002) *Biochemistry* 41:5276-82). Variations in affinity occur among the loop sequences, with SL3 and SL2 binding most tightly (See Table 1 for selected $K_d$ values and FIG. 3 for the loop definitions). The binding constants are derived from a tryptophan fluorescence assay illustrated in FIG. 5 (hereinafter, "Trp assay", "Trp-binding assay", or similar variations).

The assay is based on quenching of the fluorescence of tryptophan-37 in the protein by residues in the single-stranded RNA loops. The G318/W37 stacking in the SL3-NCp7 structure is illustrated in FIG. 4. Tightly bound RNA molecules quenched nearly all the fluorescence of NCp7 in 0.2 M NaCl. The tightest binding variant we have examined (Paoletti, A. C.; Shubsda, M. F.; Hudson, B. S.; Borer, P. N. (2002) *Biochemistry* 41, 15423-15428; "Affinities of the HIV-1 Nucleocapsid Protein for Variants of SL3 RNA."; appended hereto and incorporated in its entirety by reference thereto), SL3-GGUG, has a limiting fluorescence that plateaus at the background of the buffer (A319 is changed to U in this variant, see FIG. 3). Its binding profile approached that of a 1:1 complex with an infinite binding constant ($1/K_d$; similar to the short-dashed line in FIG. 5). In contrast, when the GGAG-tetraloop of tight-binding SL3 is replaced with UUCG or GAUA, quenching was almost nil indicating very low affinity. This is consistent with the primary event in W37 quenching being the close stacking of G318. In addition, there are primarily electrostatic interactions between the N-terminal 3-10 helix and the RNA stem (see FIG. 4). The binding site covers a substantial part of this small protein's surface.

TABLE 1

Dissociation constant and relative affinity for RNA-NCp7 complexes.

| RNA | $K_d$ (nM) | RA[a] |
|---|---|---|
| SL1a | 100 ± 10 | 28% |
| SL1I | 140 ± 20 | 20% |
| SL2 | 23 ± 2 | 120% |
| SL3 | 28 ± 3 | 100% |
| SL4 | 320 ± 30 | 9% |
| SL3-UUCG | ~7,500 | 0.4% |
| SL3-GAUA | ~16,000 | 0.2% |
| SL3-GGUG | ~3-8[b] | ~4-10x |
| SL3-all-DNA | 230 | 12% |
| SL3-(DNA stem)-(RNA loop) | ~30 | ~100% |

[a]Affinity for NCp7 relative to SL3.
[b]The values for tight-binding complexes are not well determined.

A 154mer construct (the entire sequence in FIG. 3 that includes all four stem-loops) bound tightly to NCp7. The assay indicated that the equivalent of three NCp7 molecules were bound with high affinity per RNA (see FIG. 5, where the binding isotherm intersects the axis at $R_t/P_t$≈0.33; it is possible that two strong sites and several weaker ones combine to give the appearance of three strong sites). This is the first evidence that multiple NC-interactions are likely to occur with the 5'-leader.

All but one of the earlier studies of stoichiometry and affinity were performed at ionic strengths below 0.2 M (Damgaard, C. K. et al. (1998) *Nucleic Acids Res* 26:3667-76; Shubsda, M. et al. (1999) *Biophys Chem* 76:95-115; Shubsda M. F. et al. (1999) *Biochemistry* 38:10147-57; Shubsda, M. F. et al. (2000) *Biophys. Chem.* 87:149-65; McPike, M. P. et al. (2001) *Biochemistry*; Amarasinghe, G. K. et al. (2001) *J Mol Biol* 314:961-970; Berglund, J. A. et al. (1997) *Nucleic Acids Res* 25:1042-9). However, we found unusual properties in the system at low ionic strength. This included irreproducibility of the binding isotherms, decreases in the initial fluorescence, increases in the residual fluorescence, and binding curves that can only be described by at least two binding constants. The low-salt regime appears to be dominated by nonspecific interactions between these highly charged molecules; the free protein may also be less structured at low salt. By contrast, SL3 titrations at 0.2 M NaCl (FIG. 5) were highly reproducible. The $K_d$ for SL3 in Table 1 is the average of 11 determinations with six different protein preparations (standard deviation <10%).

We found a linear salt dependence at 0.2-0.8 M NaCl (Shubsda, M. F. et al. (2002) *Biochemistry* 41:5276-82), and estimated that there are five to six ion pairs in the SL3-NCp7 complex. In agreement, the NMR structure predicts six salt-bridge interactions between basic side-chains of the protein and the RNA phosphates (DeGuzman, R. et al. (1998) *Science* 279:384-388).

SL3 variants and modified RNAs We have studied the sequence dependence of binding in about 50 variants of SL3 (Paoletti, A. C.; Shubsda, M. F.; Hudson, B. S.; Borer, P. N. (2002) *Biochemistry* 41, 15423-15428). There are 64 possible variants of the loop positions GXYZ using A, C, G, U (the first G-residue was held constant as it is not involved in the loop-NC interaction). Strong binding occurred when XYZ=GNG, but the other loop sequences were considerably weaker. Interestingly, the preferred sequence for greater affinity was that Z=G; this corresponds to G320, and is not the base that stacks on W37 (FIG. 4). A DNA 20mer version of SL3 had about 15% of the affinity of SL3 RNA.

Several changes are tolerated in the sequence that are useful in designing the fluorescence-quenching pair RNA/DNA chimeric switches of the present invention, or in designing test competitors with reduced complementarity to the switches (Paoletti, A. C.; Shubsda, M. F.; Hudson, B. S.; Borer, P. N. (2002) *Biochemistry* 41, 15423-15428). For instance, a 16mer RNA construct was found to bind NCp7 with the same affinity as the 20mer used in earlier studies (Shubsda, M. F. et al. (2002) *Biochemistry* 41:5276-82), and only the loop needs to be RNA for efficient binding (see last entry in Table 1). There was virtually no change in $K_d$ upon substituting base pairs near the loop, C316-G321→G316-C321, G315-C322→(C315-G321 or A315-U322). Also, G320→dG320 was well tolerated, and only slight reduction in affinity was engendered by substituting inosine at loop sites 317, 318, or 320.

We also studied several nucleotide DNA oligomers containing the G-X-G sequence. These have been reported (Vuilleumier, C. et al. (1999) *Biochemistry* 38:16816-25; Fisher, R. J. et al. (1998) *J Virol* 72:1902-9) to possess relatively high-affinity for NCp7. However, none of these molecules had even micromolar affinity for NCp7 at 0.2 M NaCl (Paoletti, A. C.; Shubsda, M. F.; Hudson, B. S.; Borer, P. N. (2002) *Biochemistry* 41, 15423-15428).

We mapped the affinities of the wild-type interaction sites for NCp7 in the major packaging domain of the. 5'-leader RNA (Shubsda, M. F. et al. (2002) *Biochemistry* 41:5276-82), and explored the diversity of interactions using variants of the SL3 loop. In order to design and evaluate anti-NC drugs it is useful to know the affinities the protein has for its natural substrates under physiological conditions, and to probe the nature of binding loci by systematic variation of the sequence. The results add to our understanding of RNA-protein interactions, highlighting problems that may occur when these studies are conducted at low ionic strength. We also demonstrated that multiple NCp7 proteins interacted with the major packaging domain, and that a linear G-X-G loop sequence in the RNA was not required for high affinity. A close correlation was found to exist between structural features and our rapid technique to evaluate the diversity of RNA-NC interactions.

The Trp-binding assay provided a reliable method to establish structure/free energy relationships. The simple expedient of comparing affinities at 0.2 M NaCl is sufficient to distinguish trends that are helpful in designing anti-NC agents. However, significant obstacles prevent use of the Trp-assay as a high throughput screen. (1) It is not sensitive enough to accurately measure the affinities of tight-binding complexes, where low concentrations are required for appreciable dissociation of the complex. (2) The Trp assay requires fluorescence excitation in the UV, which will restrict its application in high-throughput screening of anti-NC drug candidates. (3) A Trp-based assay is inherently less sensitive than one using dyes for labeling proteins and nucleic acids with fluorophores that absorb and emit in the visible region of the spectrum.

High-Resolution Structures

The structure of a relevant complex is an extremely valuable guide in undertaking drug-design. The structure for the NCp7-SL3 complex is presented in FIG. 4. G318 interacts in a hydrophobic cleft of F2, the upper zinc finger shown in the figure and a very similar interaction is made between G320 and F1. These two residues comprise the $G_2$-locus for the SL3 loop, and each G-base makes identical H-bonds with backbone amides and carbonyls in the fingers. Electrostatic interactions also play a role because of the high formal charges involved, +9 for $Zn_2$.NCp7 and –19 for the SL3 20mer. The electrostatic surface of the protein (not shown) has the RNA in a deep electropositive pocket on the nucleotide-binding surface of the protein. We also used NMR to determine the structure of the unbound RNA, which alters considerably upon binding the protein (Pappalardo, L. et al. (1998) *J. Mol. Biol.* 282:801-818). The structures of the finger domains are largely determined by coordination to the zinc, and do not change upon binding RNA or DNA. However, the linker and the termini are flexible in the absence of nucleic acid at low ionic strength (Lee, B. M. et al. (1998) *J. Mol. Biol.* 279:633-49). The N-terminal residues form a 3-10 helix in the complexes with SL3 and SL2; this helix interacts mainly by salt-bridge interactions with the RNA stem.

High-Throughput Assays

Our work on the RNA-NC complex is relevant to the design of high-throughput drug discovery. We have established reliable assay conditions, and describe a multiplex assay to examine many thousands of potential inhibitors. We also have completed a survey of the affinities of the most important wild-type RNA substrates for NC binding, and have explored the diversity of interactions. We have high-resolution structures to guide our search for anti-NC agents.

The design of high-sensitivity and high-throughput assays take advantage of our earlier work on the SL3-NCp7 system. The detection scheme uses highly efficient fluorophore labels similar to known molecular beacons (Tyagi, S. & Kramer, F. R. (1996) *Nat Biotechnol* 14:303-8; Fang, X. et al. (2000) *Anal Chem* 72:747A-753A). The beacons utilize the process called Fluorescence Resonance Energy Transfer (hereinafter "FRET").

Fluorescent Nucleic Acid Switches

The FRET system outlined in FIG. 6 can be configured to detect the presence or absence of NC-RNA complexes, and can be adapted to nearly any other protein-RNA or protein-DNA complex. For the SL3-NCp7 equilibrium, the SL3 RNA hairpin is available at the right of the two-headed RNA/DNA chimera, O (see panel b). This switch has fluorescent labels, * (e.g., FAM, 6-carboxy-fluorescein), at the 5'-end of the chain and Q (a quencher, e.g., dabcyl) near the 3'-end of the DNA segment (light font). Any fluorescent label and quencher now known in the art may be used in the switches of the present invention. In the O species, * and Q are within the Förster distance for efficient quenching. However, they are far apart in the extended hairpin form, H, and the switch emits strongly.

By altering the DNA sequence, $K_1$ is adjusted between 0.1-0.01 ($K_1$=[O]/[H]). This gives 90-99% of the maximal fluorescence signal in the absence of the other components. Upon addition of NCp7 (P), the $K_1$ equilibrium shifts to the right, and the fluorescence signal decreases. The switch is set to a null signal in the presence of a slight excess of P, and is triggered to emit when a competitor, C, sequesters the protein in the P.C complex. The fluorescent nucleic acid switches of the present invention share some properties with the "scorpion" probes used in real-time PCR applications (Solinas, A. et al. (2001) *Nucleic Acids Res* 29, E96; Thelwell, N. et al. (2000) *Nucleic Acids Res* 28:3752-61). Knowledge of $K_1$, $K_2$, and the input concentrations, $O_t$, $P_t$, and $C_t$ will allow estimation of $K_3$.

The bistable nature of the free switch and switch-protein complex is related to thermodynamic properties. The populations of the species will reach an equilibrium state that can be predicted with confidence from thermodynamic databases (Sugimoto, N. et al. (1995) *Biochemistry* 34:11211-6; Santa-Lucia, J. (1998) *Proc Natl Acad Sci USA*, 95, 1460-1465; Mathews, D. H.; Sabina, J.; Zuker, M.; Turner, D. H. (1999) *J Mol Biol* 288, 911-940; Zuker, M. (see web site: bioinfo.math.rpi.edu/~zukerm). The procedure is analogous to using two entries in the free energy tables in a physical chemistry text to predict the equilibrium constant for a third reaction. While such tables in chemistry texts are often accurate to 0.01 kcal/mol, the DNA/RNA databases have uncertainties on the order of 1 kcal/mol. That is enough to change the populations of the free and protein-bound switches by nearly an order of magnitude. However, as shown in Table 2, a few changes to the sequence can change $K_1$ by twelve orders of magnitude. Therefore, one of skill in the art could readily fine-tune the equilibrium constant $K_1$ by changing the sequence, and then monitoring the populations of the two species by measuring fluorescence in accordance with the present teachings.

A multiwell, array or microarray format may be applied in accordance with one preferred embodiment of the present invention to screen small-molecule inhibitors for their potential to bind NCp7 or NC-containing precursors. It can be determined whether a compound permanently inactivates P or O, or releases the fluorophore by hydrolysis of the nucleotide chain. Titrations or bracketing tests can be used to classify "hits" in these screening assays. Hits will also be subjects for a "minus P" control; interference from competitor-nucleic acid interactions might be apparent from adding competitor to a flourescent switch with $K_1$=10-100. Changing the location of the quencher to the 3'-end of the RNA segment can also be used to make confirmatory tests. In that case, the O form is highly flourescent, and the assay will show a null for effective competitors,

TABLE 2

Predicted K1 and mismatch sites for four molecules compared to the fully paired H chimera, M1*

|   |    | M1 | M2 | M3 | M4 | M5 |
|---|----|----|----|----|----|----|
|   | $K_1$ | $6 \times 10^{-9}$ | $4 \times 10^3$ | 0.08 | 0.003 | 0.002 |
| P | 3  |    | T  | A  |    |    |
| O | 4  |    | A  | T  |    | T  |
| S | 5  |    | G  |    | T  |    |
| I | 8  |    | A  | T  |    |    |
| T | 9  |    | C  |    |    | AAA |
| I | 12 |    | C  |    | A  |    |
| O | 13 |    | T  | A  |    | A  |
| N | 14 |    | A  | T  |    |    |

*Blank entries signify that the site has the same base as in M1.

Bistable A1/A2-constructs can be designed to detect competitors for other A2-L or A1-L complexes other than the HIV-1 nucleocapsid protein. Applications include RNA-protein interactions where the RNA binding site can be designed into the O-form. These include the RRE-rev and TAR-tat RNA-protein complexes in HIV-1. Other competitors of naturally occurring DNA-protein or RNA-protein complexes can be designed where the favored binding site for L occupies an analog of the O— or H-form. This design feature of the present disclosure distinguishes it from approaches based on combinatorially-derived sequences. However, the use of empirically chosen, rather than engineered, ligand binding domains is not precluded.

RNA or DNA molecules referred to as "aptamers" can be selected to bind nearly any protein or other molecular target (Jayasena, S. D. (1999) *Clin. Chem.* 45:1628-1650). An aptamer or other combinatorially-derived sequence binding site can be included in the A1- or A2-form, as well. The use of combinatorial technology to develop high affinity DNA- and RNA-protein binding sites represents an alternative to naturally occurring DNA- and RNA-protein binding sites described above. It is contemplated that high-throughput screens based on our invention can be developed for a wide array of therapeutic targets, remediation of bioterror agents, and other applications. It is also contemplated that sensitive and specific ligand-detection assays based on our invention could be developed for a wide array of proteins, nucleic acids, saccharides, toxins, and other molecules of diagnostic importance in humans, animals, plants, and other organisms, as well as for nearly instantaneous and specific assays for bioterror agents, and other applications.

Simple modifications to the scheme just described are required for the diagnostic applications. A competitor, C, does not need to be present for most diagnostic applications, in which case the K3 equilibrium in FIG. 6a is removed from consideration. The ligand-detection assay should give a minimal signal in the absence of L, and a strong signal when there is a substantial amount of the A2-L bound complex. One suitable alteration moves the quencher, Q, to the right-hand end of the chains shown in FIG. 6b. Then the H-form has a minimal signal because a fluorophore is near in space to a quencher. By contrast, the O-form is highly fluorescent because the quencher is situated beyond the distance for efficient suppression of the signal. Other arrangements of fluorophore and quencher can be contemplated that would be useful to detect the state change.

Design Parameters for Fluorescent Nucleic Acid Switches

The NC binding site A basic design feature illustrated in FIG. 6 is to provide the highest affinity $G_2$-locus in the RNA loop with a stem identical to SL3; this feature is present at the right side of O in the figure. At the same time, the DNA and RNA hairpin loops are complementary to each other; GGUG will be double-stranded in H, and therefore unavailable to bind NC. The single-stranded DNA loop in O will not compete for NC, as we have shown that C-rich loops, and DNA loops in general, have much lower affinity (~10,000 times less for these d(CACC) loops). Note that we have chosen the GGUG loop sequence, which binds NCp7 more tightly than the wild-type GGAG (see Table 1; $K_2$ and $K_3$ are dissociation constants for the relevant complexes in this text).

Tuning the K1 equilibrium. The switch design will preferably aim for $0.01<K_1<0.1$ in the fluorescence assays. A small $K_1$ value favors the "bright" H conformation, and will give a near maximal signal-to-noise ratio (S/N) when the system switches from the "dark" PO form. However, $K_1$ should not be too small or an extremely high affinity $K_2$ will be necessary to switch to PO. That is because the second equilibrium is concentration-dependent, and $O_t$ and $P_t$ will be ~0.1-10 μM. Preferred S/N will result if $[H]/([O]+[PO])>3$ at reasonable $P_t$ values in the presence of an interesting competitor. Thus, when $K_2$ is ~10-20 nM, $K_1$ is preferably set to trip the switch from off to on over a small increase in $C_t$.

The $K_1$ equilibrium is adjusted by changing the sequence of the DNA part of the strand, particularly near positions 4, 8, or 13 (see FIG. 6b). When these residues are all complementary to their RNA counterparts, H has four base pairs more than are present in the DNA and RNA stems of O. Then H will dominate the $K_1$ equilibrium. The stabilities, $\Delta G°(H)$ and $\Delta G°(O)$, can be estimated from thermodynamic databases (Sugimoto, N. et al. (1995) *Biochemistry* 34:11211-6) for forming a folded structure of DNA, RNA, or a DNA/RNA hybrid from the unstructured coils. The difference in free energy for the two forms is $\Delta G_1° = \Delta G°(O) - \Delta G°(H)$ since their unstructured reference states are identical. We have estimated the free energy for 22 sequences and find that by forcing mismatches in H that are compensated in O, $K_1$ can be varied over 12 orders of magnitude. Several of these put $K_1$ in the preferred range for the applications disclosed herein. There is uncertainty in applying the databases to these molecules, especially for the effect of mismatches in RNA-DNA hybrids, and adjusting the calculations to 0.2 M NaCl. Even so, it should be within the ability of a skilled person in this field to construct an O ⇔ H system with the desired properties starting from the disclosed predictions.

Table 2 provides guidance to the skilled practitioner in calibrating the $K_1$ equilibrium. The bright state, H, has been characterized as the fully paired 40mer, M1, with * and Q as in FIG. 6b. and the properties of the dark state were demonstrated by the M2 molecule, which favors O by a factor of ~4000 over H. The latter has $K_2$ similar to that of SL3 RNA; this was tested using the Trp-assay. The fluorescent switches, M2-M5, should be bright in the absence of NCp7 and dark in its presence (this has been verified for M2). Each of the molecules disclosed herein has been tested with MFOLD (see web site: bioinfo.math.rpi.edu/~zukerm) to ensure that no alternative secondary structure will be present. Note that the lengths of the base-paired stems, exact positions of the fluorophore and quencher, and detailed sequence can vary from that presented for M1 through M5, and still fall within the bistable H/O classification encompassed within this disclosure.

The full sequences for M1-M5 chimeras (SEQ ID Nos. 1-5, respectively) are:

```
                                           (SEQ ID NO: 1)
M1 = FAMd(GCTAGCCACCGCTAGC(T-dabcyl)CCAACACGC)-
UAGCGGUGGCUAGC;

(SEQ ID NO: 2)
M2 = FAM-d(GCATGCCTCCGCATGC(T-dabcyl)CCAACACGC)-
UAGCGGUGGCUAGC;

(SEQ ID NO: 3)
M3 = FAMd(GCTATCCACCGATAGC(T-dabcyl)CCAACACGC)-
UAGCGGUGGCUAGC;

(SEQ ID NO: 4)
M4 = FAM-d(GCTTGCCACCGCAAGC(T-dabcyl)CCAACACGC)-
UAGCGGUGGCAUGC;
and (SEQ ID NO: 5)
M5 = FAM-d(GCTAGCCAAAACGCTAGC(T-dabcyl)CCAACACGC)-
UAGCGGUGGCUAGC.
```

The DNA residues are denoted by "d(XXX)" and RNA residues are not enclosed by parentheses; sequence alterations from M1 (also shown in FIG. 6) are underlined. The fluorophore (FAM=6-carboxymethylfluorescein) and universal quencher (dabcyl) are well-known to practitioners skilled in FRET technology. The FAM label can be attached via a 5'-phosphate at the 5'-end of the DNA chain, T-dabcyl derives from the replacement of the 5-methyl of T by dabcyl (methyl red); both dyes can be incorporated via ordinary solid-phase coupling or modification after solid-phase synthesis using standard methods.

It is likely that the databases can predict only the order of magnitude of $K_1$. Therefore, experiments with two to four mismatched variants may be required to tune the assay for optimal switching performance. It is likely that the order of free energies predicted from the databases is correct, even if the actual values are not. For instance, if $K_1$ is found to be too small for best performance, a molecule predicted to favor O more strongly can be substituted.

One could have a concern that the switches might dimerize. However, when the dimerization equilibrium constant is estimated from the thermodynamic databases, and the concentrations for the fluorescence applications are used, the amount of such dimers is vanishingly small.

Simulating the binding equilibria. Optimizing performance of the assays and analyzing the results is greatly assisted by simulations with input values of $K_1$, $K_2$, $K_3$, $O_t$, $P_t$, and $C_t$. The coupled equilibria describing all of the species result in a cubic equation for the fluorescence competitor assay. This requires special treatment to solve for roots that are physically reasonable and that allow continuous variation of $C_t$ or other species in simulating titrations (Press, W. H. et al. *Numerical Recipes*, Cambridge U. Press, New York, 1986).

FIG. 7 illustrates the performance characteristics of a high throughput screening assay. At the dashed vertical line, $C_t = 10$ μM, which is often used for testing libraries of chemical compounds. The simulations are helpful in adjusting the assay conditions for lower or higher-affinity competitors, other concentrations of competitors, etc.

Dynamic range is a function of the input variables $K_1$, $K_2$, $O_t$, $P_t$, and $C_t$. Under the conditions at the dashed line in FIG. 7, a dynamic range of 100 in $K_3$ can be distinguished in one well of a microtiter plate. Other wells can have other values for the input parameters. A dynamic range of 10,000 is reasonable for two or more wells per sample.

For low-affinity inhibitors, high concentrations are required and sensitivity is not an issue. Sensitivity is important for fluorescence assays of the present invention only when the inhibitor affinity is so high that very low protein and inhibitor concentrations are needed to force appreciable dissociation of the complex. At that point, it is not necessary to measure an exact $K_d$—instead, one may need ADME/Tox assays to determine whether this is a bona fide drug lead.

Synthetic considerations The fluorescent chimeric RNA/DNA switches are made in two pieces. The "left-oligo" (left side of the double-headed "Orthos" molecule in FIG. 6b) is composed exclusively of DNA, contains both the * and Q labels, and has a free 3'-OH. The right-oligo is 5'-p-d(ACGC)-(RNA14mer). The two pieces are ligated against a DNA splint strand using T4-DNA ligase (Moore, M. J.; Query, C. C. (2000) 317, 109-123.). The splint is complementary to the DNA linker (L in FIG. 6b), and the 5'-side+loop sequence of the RNA. We have achieved >50% ligation efficiency, using 5'-p-d(AC)-RNA; this is already efficient enough for the amounts needed for FRET assays. However, we also found that only the SL3 loop needs to be RNA for efficient NCp7 binding (last entry in Table 1). By increasing the number of DNA bases near the linker, ligation efficiency may be improved. The splint has been checked with MFOLD to ensure that it has no stable self-structure that is likely to impair its application in ligation.

The labeled full-length 40mer chimeras can also be purchased. However, they are very expensive, and require postsynthetic modification to attach one of the labels. These steps are never as efficient as stepwise phosphoramidite synthesis, and it can be problematic to purify doubly labeled material for longer oligonucleotides. By contrast, each of the halves can be prepared from the amidites, and we routinely purify ~20mer length molecules by anion-exchange HPLC. Reversed-phase HPLC is also useful for purifying fluorescently tagged oligomers from unlabeled versions. After ligating the halves, highly pure material can be prepared using conventional methods, e.g., by either denaturing PAGE or HPLC.

The extra flexibility in assembling the chimeras will prove valuable. The RNA side has only one sequence—GGUG. It will be useful to have many sequences available for the DNA side to facilitate calibrating the $K_1$ switch at different levels. This may also be useful in ranking competitors in several categories that differ in $K_3$.

Based on fluorescence quantum yields, the signal from the fluorescein analog, FAM, in the switches of the present invention will be 20-50 times larger per photon absorbed than for our standard Trp-assay. A visible wavelength laser can be used to excite FAM, whereas a lower intensity UV lamp must be used for Trp. Detection also has a reduced background for visible compared to UV emission. Therefore, we can expect that signal/noise ratios for unquenched FAM will be 100-1000 times larger than for unquenched Trp. This should give it sensitivity close to $^{32}$P-labeling, without radiation concerns or the approximations that are required to interpret filter-binding assays.

We have examined DNA analogs of the two extreme states in FIG. 6b (sequences M1 and M2 in Table 2). They differ by a factor of 10 in fluorescence intensity. This allows the equilibrium shift upon changing the sequence, or adding NCp7, to be monitored very easily. Simply put, the fluorescence of pure H and O are known, so their populations in a mixed system will be just a linear function of the measured fluorescence.

Improvements may be effected by using a construct that brings the * and Q labels closer together in the O-state, or introduces a fluorophore-quencher pair that more efficiently suppresses fluorescence at short distances (Integrated DNA Technologies, (www.idtdna.com); Coty, C. (2002) *Drug Discovery & Development* 5: 44-51; (www.nanoprobes.com). Even at 10-fold, the sensitivity of the experiment is far higher than for the Trp-quenching assay. Another possible mode of the present invention is to use the difference in fluorescence lifetimes of the free and protein-bound switch. One expects the fluorophore to have a longer fluorescence lifetime when bound to NC than when it is free in solution. With phase modulation methods (modulated light intensity and a lock-in amplifier) one can get a steady state signal that attenuates the contribution from the short time component. Although there are commercial applications of phase modulation technology in high-throughput screening (Kashem, M. A. (2001) $5^{th}$ Intl. Drug Disc. Prod. Users Mtg; (www.zymark.com); www.moleculardevices.com), use of phase modulation in preferred embodiments of the present invention are expected to yield an increase in on/off discrimination of about 100-fold.

Other fluorophore quencher pairs which may be used in accordance with preferred embodiments of the present invention include those listed in the Integrated DNA Technologies catalog (www.idtdna.com/program/catalog/DNA_Probes_main.asp) and the Molecular Probes catalog (www.probes.com/servlets/masterlist). Of particular utility in construction of the switches disclosed herein are the following quenchers: dabcyl, BHQ-1, BHQ-2, Iowa Black, and Nanogold, and the fluorophores, 6-FAM, TET, HEX, Cy3, Cy5, eosin, coumarin, Oregon Green, Rhodamine Green, Rhodamine Red, Texas Red, TAMRA, ROX, JOE, Bodipy dyes. Of course any other quenchers known in the art are also considered applicable to construction of the fluorophore quencher pairs disclosed herein.

Others have proposed bimolecular RNA-RNA or DNA-DNA probes that could produce similar results to the unimolecular switches disclosed herein for high-throughput screens (Jayasena, S. D. (1999) *Clin. Chem.* 45:1628-1650). However, there is the unavoidable fact that the kinetics of forming the complex are second-order, and thus concentration dependent. For example, when we used a bimolecular system (i.e., removing the L-AC linker in FIG. 6b), we found that at the low concentrations typically used in fluorescence assays, the time for nearly complete equilibration was ~10 hr at room temperature. While a high-throughput assay for competitors is still possible, it would require either a long equilibration time, or annealing by heating. It would be preferable to avoid heating. Using bimolecular probes it may be awkward to perform titrations for determining accurate $K_3$ values. Simulations may also be more difficult, involving equations that are fifth-order in some of the variables. This may make designing the assays more difficult, as well as complicating interpretation of the results.

There is another aspect of kinetics that may be significant in regard to certain aspects of the present invention. For example, with respect to the bistable unimolecular switches of the present invention, the system must go through a partially paired intermediate to convert from one state to the other. There will be an associated activation barrier that slows the conversion between the two forms. The barrier probably depends on the length of the stems in the hairpins. Therefore, we prepared a 16mer SL3 construct, which has two base pairs removed from the 20mer SL3 stem used previously. The Trp-assay showed that both have virtually identical $K_d$ values. The 16mer has been incorporated in a preferred embodiment of the fluorescent switch design (FIG. 6), and we have shown that equilibration with NCp7 has been shown to occur within a minute at a 10 nM concentration of the M3 switch. Another aspect favoring rapid equilibration across $K_1$ is the chaperoning aspect of NCp7, which allows even lambda DNA to quickly adjust to its lowest free energy form under force-induced stretching.

Competitor Binding

The experiments outlined below move from applications of known competitors of the NC-RNA complex to those that have the potential to become useful drugs directed against new anti-HIV targets.

Ligands with known affinity The Trp-assay cannot determine the affinities very well for tight-binding ligands of NCp7. Reviewing FIG. 5 reminds us that titrations for such ligands will deviate only slightly from the dashed 1:1 line for $K_d=0$. The deviation is largest when the complex approaches saturation, so only a few data points control the value determined for $K_d$. Since the deviation and the S/N are small for these points, the effect of experimental errors is large.

The fluorescence-quenching assays using the switches of the present invention offer a method to determine $K_d=K_3$ by competition, such as with SL3-GGAG or SL3-GGUG. As shown in FIG. 7, the assay is capable of determining $K_3$ accurately. The assay effectively balances $K_3$ against $K_2$ and $K_1$, so a titration provides many high S/N data points. The $K_d$ values for the RNA molecules listed in Table 1 are determined by competition with NCp7/SL3-GGAG. The results match or improve the $K_d$ values that have already been measured by the Trp-assay. The molecules in Table 1 that have the SL3 stem are modified to avoid extensive complementarity to the DNA side of O.

Measurements of unknown affinities RNA aptamer constructs selected against NCp7 for which nanomolar affinities have been asserted from measurements at low salt concentrations (Lochrie, M. A. et al. (1997) *Nucleic Acids Res* 25:2902-10; Berglund, J. A. et al. (1997) *Nucleic Acids Res* 25:1042-9; Allen, P. et al. (1996) *Virology* 225:306-15), have been studied with our tryptophan assay. The aptamer construct sequences have been published, and appropriate RNA molecules are available commercially, which were purified by standard methods. Some of these aptamer constructs do not have obvious $G_2$-loci, and could be very useful in expanding our general understanding of the basis for NC-RNA binding specificity. However, we have shown that all of the published aptamer constructs bind two or more NCp7 proteins per RNA, rendering them marginally useful in drug discovery applications. Other RNA constructs we have inferred from aptamer sequences have 1:1 stoichiometry and affinity for NCp7 that is similar to SL3 and SL2.

The cyclic peptide, c(F-C-dW-R-C-K), has been shown to have effects that suggest it competes with NCp7 (Druillennec, S. et al. (1999) *Proc Natl Acad Sci USA* 96:4886-91). This fluorescence-quenching assay is not done in the competition mode described above. Instead, the quencher is located at the 3'-end of the 40mer chain, and the dominant H-species will be dark. If the peptide binds to O, the switch will light and allow measurement of $K_d = K_2$. If the c(F-C-dW-R-C-K) competition is favorable, other cyclic peptides may be used in accordance with this embodiment of the present invention.

The competitor binding tests allow us to measure affinities of compound libraries in a high-throughput fashion. They also provide a means to determine whether designed or combinatorial changes improve the affinity of anti-NC candidates.

Other Target Interactions

In addition to the interactions between the viral RNA and the NC domain characterized above in development of the chimeric switches of the present invention, any other target interactions with RNA, DNA, proteins, precursors, and saccharides may be exploited in accordance with the present disclosure. Some of these targets include, without limitation, the internal ribosome entry site (IRES) of Hepatitis C Virus, IRES sites in other viruses, as well as agents involved in the etiology of viral infections related to Congo-Crimean hemorrhagic fever, Ebola hemorrhagic fever, Herpes, human cytomegalovirus, human pappiloma virus, influenza, Marburg, Q fever, Rift valley fever, Smallpox, Venezuelan equine encephalitis, and targets in HIV-1, MMTV, HIV-2, HTLV-1, SNV, BIV, BLV, EIAV, FIV, MMPV, Mo-MLV, Mo-MSV, M-PMV, RSV, SIV, AMV, and other related retroviruses, including but not limited to: TAR-tat, RRE-rev, DIS, PBS, RT, PR, IN, SU, TM, vpu, vif, vpr, nef, mos, tax, rex, sag, v-src, v-myc and precursors and protease products of the precursors: gag, gag-pol, env, src, onc, as collected in Appendix 2 of (Coffin, J. M., Hughes, S. H., Varmus, H. E. (1997) Retroviruses, Cold Spring Harbor Lab Press, Plainview, N.Y.). Other targets in bacteria, fungi, insects, and other pathogens and pests of humans, animals, and plants may also be applicable to the present switches and methods, including but not limited to *B. anthracis*, (especially the components of the toxin: protective antigen, lethal factor, edema factor, and their precursors), *Burkholderia pseudomallei*, Botulinum toxins, Brucellosis, *Candida albicans*, Cholera, *Clostridium perfringins* toxins, Kinetoplasts, Malaria, Mycobacteria, Plague, Pneumocystis, Schistosomal parasites, *Cryptosporidium, Giardia*, and other environmental contaminants of public and private water supplies, Ricin, Saxitoxin, Shiga Toxin from certain strains of *E. coli*, *Staphylococcus* (including enterotoxin B), *Trichothecene mycotoxins*, Tularemia, and agents causing Toxoplasmosis, as well as contaminants of food and beverages that may be deleterious to human or animal health. The detection and screening methodologies afforded by some embodiments of this invention may also be applied to small-molecule targets, including but not limited to nerve gas agents and chemical poisons, as well as contaminants of public and private water supplies, of food and beverages, and of indoor air that may be deleterious to human or animal health.

Certain molecular electronic applications can be realized using an embodiment of the present invention. This application also serves to illustrate methodology for integrating combinatorial sequence technology with H to O switching. For example, FIG. 8 outlines the heart of a Read/Write/Erase device for information storage. The top panel indicates that the oligonucleotide-fluorophore/quencher "switch" can exist in a "zero" or a "one" conformation that can be toggled by light of frequencies, ν1 and ν2. The state of the switch can be interrogated by light at ν3; the zero state has a very low fluorescence emission at ν4, while the one state has robust emission. The device has only Read/Write capability if the zero to one conversion is not capable of being reversed by ν2. (The energy of a photon is represented by hνi, where Planck's constant is h. The wavelength of light is $\lambda i = c/\nu i$, where c=speed of light.)

The bottom panel of FIG. 8 illustrates an embodiment of the principles just discussed. An H-type molecule, similar to that in FIG. 6, is shown attached at its bottom to a solid support (S); such a solid-support attachment may be useful in some applications of the technologies described for diagnostics and screening presented previously. In molecular electronic applications this attachment provides spatial addressability. The embodiment illustrated in FIG. 7 has a very similar arrangement of fluorophore (*) and quencher (Q) to that illustrated in FIG. 6, and it can be seen that H to O conformational equilibria are still common features. However, a difference lies in the attachment of a photosensitive chemical entity to the 3'-end of the RNA/DNA chain by a flexible linker. The photochemical entity is illustrated in the figure as having two states, L1 which is converted to L2 by irradiation at ν1; if the erase function is to be implemented, L2 must be capable of efficient back conversion by the action of ν2. When the photochemical entity is in the L2 state, the O2 to H2 equilibrium will favor H2, just as in the screening interaction illustrated previously, and intense fluorescence will occur due to the long distance between * and Q. Only the O-form of the construct has a combinatorially-derived sequence binding pocket with high affinity for L1, but low affinity for L2. Thus, prior to irradiation at ν1, the binding free energy of L1 for the binding pocket drives the equilibrium to favor the "dark" O1-form with very low fluorescence emission. Although there are four states illustrated in FIG. 8, the concentrations of the H1 and O2 states will usually be very small; they are essentially intermediates in the pathway to converting between the stable O1 and H2 forms.

Molecules known as fulgides and fulgimides can exist in states where a central ring is open or closed photochemically. The forms can be cycled many times by the action of light at two different wavelengths (Wolak, M. A. et al. (2002) J. Photochem. Photobiol. A, 147:39-44). Many other photochemical entities have been characterized, as well (Willner, I. (1997) Acc. Chem. Res., 30:347-356). An o-nitrobenzyl photochemistry (Zhang, K. & Taylor, J.-S. (2001) Biochemistry, 40:153-159) is particularly useful for Read/Write (no erase) devices. Here the action of light at λ1=365 nm cleaves the L1 ligand from the 3'-end of a DNA molecule. After cleavage, the effective concentration of L1 near the binding pocket is reduced by a large fraction, rendering the switch in the permanently "on" H-form.

Such devices are quite practical for sensitive Read/Write information storage applications. The domain size for fluorescence detection and writing using laser light sources is limited only by diffraction at the wavelength used. Usually many fewer photons will be required for reading (fluorescence) than for writing or erasing (photochemical rearrangement of bonds). Therefore, it is unlikely that reading will cause a sufficient amount of photochemistry to practically reverse the writing and erasing steps. A single addressable domain may contain molecules with different photochemical ligands, L1/L2. This can be used to provide wavelength discrimination within a domain in a manner similar to current plans for holographic data storage devices (Wise, K. J. (2002) Trends Biotechnol. 20:387-394). Likewise, different fluorophores with distinct absorption and emission spectra can provide multicolored detection.

Other arrangements of fluorophore, quencher, binding pocket, and molecular conformation are possible for such switching devices within the scope of the present disclosure. It is also not a general requirement that the nucleic acid portion be chimeric for many applications involving combinatorially-derived sequence binding pockets.

Another embodiment of the invention disclosed herein is to insert the switchable element within a closed circular DNA double helix. Supercoiling in DNA is well-known (Cantor, C. R. & Schimmel, P. R. (1990) Biophysical Chemistry Part III, 1265-1290). It is easy to control the density of superhelical turns using intercalating dyes and topoisomerase enzymes (Wang, J. C. (1996) Annu. Rev. Biochem. 65:635-92; Wang, J. C. (1984) J. Cell Sci Suppl. 1:21-29). The helical nature of double-stranded DNA engenders a substantial resistance to supercoiling; this resistance can be tapped to switch the state of a localized domain to reduce the superhelical stress. The resistance can be quantified by a free energy, $\Delta G°(sup)$, which expresses the ability to cause chemical change upon relaxing the superhelical turns.

For example, the molecule at the left of FIG. 6b could be joined to a long DNA double helix below the bottom G-C base pair, and the upper loop removed so that the top C-G base pair was joined to another long DNA double helix above. The ends of these long DNA segments could be covalently joined to make an interwound pair of circles with the DNA side of the switch region on one strand, and the RNA side on the other. If the circular DNAs are twisted in the proper superhelical direction, enough energy can be stored to cause a local cross-shaped, "cruciform" that extrudes the two loops—the boxed GGUG sequence and its complement CACC. This comes at a cost in free energy, $\Delta G°(cru)$. That is because now four base pairs are lost for the two tetraloops, and there is additional disruption at the branch of the cross. When $\Delta G°(sup)$ has a large enough magnitude, the $\Delta G°(cru)$ penalty is overcome, and the cruciform extrudes. The point at which cruciform structures and double helix have equal populations in equilibrium is when $\Delta G°(cru)=\Delta G°(sup)$.

This sets up a very similar situation to that described above, where the K1 equilibrium constant was adjusted by changing the nucleic acid sequence to set the trigger for a large change in fluorescence (O→H) to occur upon addition of a small amount of an effective competitor, C. If a ligand, like NCp7, is present in high enough concentration with the superhelical switch, it will bind the GGUG tetraloop and force the cruciform to occur at a lower density of superhelical turns. This can be quantified using free energies, which are additive; now the equal balance between cruciform and double-helical structures occurs when $\Delta G°(cru)=\Delta G°(sup)+\Delta G(NC/GGUG)$. The balance between the two sides of this equation can be adjusted so that addition of a small amount of competitor ties up enough NC to reduce the $\Delta G(NC/GGUG)$ contribution, and switch the state away from the cruciform state. The adjustment in this case is accomplished by changing $\Delta G°(sup)$, which is a simple function of the number of superhelical turns. Sequence-based tuning, as illustrated earlier, combined with balancing via superhelix density is attractive for the development of suitable bistable constructs. Current procedures for creating superhelices create a range of superhelix densities and relaxed molecules; it may prove necessary to purify constructs with a relatively small range of superhelix densities.

Readout of the state of the cruciform/helix switch can again be accomplished by fluorophore-quencher pairs. If these are positioned near the cruciform tetraloops, the cruciform state will be highly fluorescent and the helix form dark. Positioning * and Q near the ends of the DNA side (analogous to FIG. 6) will produce the opposite result.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A unimolecular bistable molecular switch comprising a nucleic acid comprising a binding domain for a ligand, a framework and a signaling apparatus comprising an attached fluorophore and a quencher, and which alters reversibly between a state H, a state O and a state OL according to the reaction scheme,

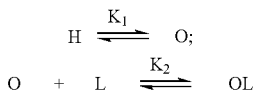

wherein each state of the switch consists of a single predominant secondary structure;
wherein state H represents the molecular switch when the ligand binding domain (LBD) is hidden comprising a first stem loop portion which comprises a first stem segment and a second stem segment, wherein the first and second segments connected by a first loop portion form a first stem portion that disrupts the secondary structure of the LBD that is preferred for binding the LBD to the ligand;
wherein state O represents the molecular switch when the LBD is open comprising a second stem loop comprising a second loop portion and a second stem portion and a third stem loop comprising a third loop portion and a third stem portion, wherein the third stem loop comprises the secondary structure of the LBD that is preferred for binding the LBD to the ligand, and wherein the second stem loop is connected to the third stem loop by a single-stranded nucleic acid segment, wherein the single-stranded nucleic acid segment corresponds to the first loop portion of state H;
wherein state OL represents the molecular switch bound to the ligand, L, according to $K_2$, the equilibrium constant for binding O to L;
wherein the first stem loop portion comprises 2-5 mismatches which are compensated in O, whereby[O]/[H]is 0.01 to 0.1;
wherein the signaling apparatus produces a different signal in state H than in state O or OL; and
wherein the nucleic acid sequence is selected from the group consisting of SEQ ID Nos. 1, 2, 3, 4 and 5.

2. The bistable molecular switch of claim 1, wherein the signaling apparatus comprises a first reporter on the first stem segment and a second reporter on the first loop portion.

3. The bistable molecular switch of claim 2, wherein the first reporter is a fluorophore and the second reporter is a quencher of said fluorophore.

4. The molecular switch of claim 1, wherein said switch includes one or more modified nucleotide monomers.

5. The molecular switch of claim 1, wherein said LBD comprises a naturally-occurring RNA binding site or analog thereof.

6. The molecular switch of claim 1, wherein said switch exhibits a binding affinity for said ligand of Kd<1 µM.

7. The molecular switch of claim 1, wherein said ligand is from HIV-1.

8. The molecular switch of claim 1, wherein said LBD is adapted to bind NCp7.

9. The molecular switch of claim 1, wherein said ligand is involved in the etiology of HIV-1 infection.

10. The molecular switch of claim 1, wherein said ligand is derived from a pathogen.

11. The molecular switch of claim 1, wherein K1=0.002 to 0.1.

12. A diagnostic method for detecting the presence of a ligand molecule in a sample, comprising the steps of:
providing a bistable molecular switch according to claim 1;
contacting said molecular switch with said sample; and
monitoring changes in the signal.

13. The diagnostic method of claim 12, wherein the signaling apparatus comprises a first reporter on the first stem segment and a second reporter on the first loop portion.

14. The diagnostic method of claim 13, wherein the first reporter is a fluorophore and the second reporter is a quencher of said fluorophore.

15. The diagnostic method of claim 12, wherein said switch includes one or more modified nucleotide monomers.

16. The diagnostic method of claim 12, wherein said LBD has an affinity for said ligand of at least Kd<1 µM.

17. The diagnostic method of claim 12, wherein said ligand is an infectious organism.

18. The diagnostic method of claim 17, wherein said method is adapted for use in a field kit for real-time detection of said infectious organism.

19. An assay method for discovering a chemical entity that interferes with a natural RNA or DNA for binding of a ligand, comprising the steps of:
providing a bistable molecular switch according to claim 1;
contacting said molecular switch with said ligand in the absence of the chemical entity, and monitoring the signal;
contacting said molecular switch with said ligand in the presence of the chemical entity, and monitoring the signal; and
comparing the signals generated in the presence and absence of the chemical entity to determine whether the chemical entity interfered with the binding of said ligand.

20. The assay method of claim 19, wherein the signaling apparatus comprises a first reporter on the first stem segment and a second reporter on the first loop portion.

21. The assay method of claim 20, wherein the first reporter is a fluorophore and the second reporter is a quencher of said fluorophore.

22. The assay method of claim 19, wherein said switch includes one or more modified nucleotide monomers.

23. The assay method of claim 19, wherein said ligand is a viral protein.

24. The assay method of claim 19, wherein the step of contacting said molecular switch with said ligand in the presence of the chemical entity, further comprises allowing said molecular switch and said ligand to equilibrate prior to adding the chemical entity.

25. The assay method of claim 24, wherein said molecular switch is adapted to generate a null fluorescent signal upon equilibration with said ligand.

26. The assay method of claim 19, wherein said molecular switch is bound to a solid substrate in a multiwell dish, an array or a microarray.

27. A method of designing a bistable molecular switch according to claim 1 comprising introducing a mismatch of a base pair.

28. The method of claim 27, wherein the mismatch occurs in a stem structure.

29. The method of claim 27, wherein $K1=0.002$ to $0.1$.

30. A molecular switch, comprising a nucleic acid sequence selected from the group consisting of SEQ ID NOS: 1, 2, 3, 4 and 5.

* * * * *

UNITED STATES PATENT AND TRADEMARK OFFICE
CERTIFICATE OF CORRECTION

PATENT NO. : 7,718,784 B2
APPLICATION NO. : 10/544591
DATED : May 18, 2010
INVENTOR(S) : Borer et al.

It is certified that error appears in the above-identified patent and that said Letters Patent is hereby corrected as shown below:

Page 2, Column 1, Line 17, "Other Publications," "Bichem. Biophys. Res. Comm.," should be changed to --Biochem. Biophys. Res. Comm.,--

Column 2, Line 64, "*Clostridium perfringins*," should be changed to --*Clostridium perfringens*,--

Column 4, Line 54, "the RNA 5'leader." should be changed to --the RNA 5'-leader.--

Column 6, Line 36, "sequence sequence" should be changed to --sequence--

Column 7, Line 11, "in the inmediate future." should be changed to --in the immediate future.--

Column 8, Line 16, "N-ethylnaleimide (NEM)" should be changed to --N-ethylmaleimide (NEM)--

Column 11, Line 34, "and annuity of NC" should be changed to --and affinity of NC--

Column 12, Line 38, "bThe values for" should be changed to --$^{b}$The values for--

Column 15, Line 43, "to a flourescent switch" should be changed to --to a fluorescent switch--

Column 15, line 56, "is highly flourescent," should be changed to --is highly fluorescent,--

Column 17, Line 47, "M3 = FAMd (GCTAGCCACCGCTAGC" should be changed to

--M3 = FAM-d (GCTAGCCACCGCTAGC--

Column 17, Line 53, "FAMd (GCTA*T*CCACCG*A*TAGC" should be changed to

--FAM-d (GCTA*T*CCACCG*A*TAGC--

Column 17, Line 58, "UAGCGGUGGCAUGC;" should be changed to --UAGCGGUGGCUAGC;--

Signed and Sealed this

Ninth Day of November, 2010

David J. Kappos
*Director of the United States Patent and Trademark Office*

Column 17, Line 67, "*perfringins* toxins," should be changed to --*perfringens* toxins,--

Column 29, Line 51, "whereby[O]/[H]is" should be changed to --whereby [O]/[H] is--

Column 30, Line 14, "from HIV-1." should be changed to --NC from HIV-1.--

SEQUENCE LISTING

```
<160> NUMBER OF SEQ ID NOS: 9

<210> SEQ ID NO 1
<211> LENGTH: 40
<212> TYPE: DNA
<213> ORGANISM: Artificial Sequence
<220> FEATURE:
<223> OTHER INFORMATION: synthesized beacon
<220> FEATURE:
<221> NAME/KEY: misc_feature
<222> LOCATION: 1
<223> OTHER INFORMATION: FAM
<220> FEATURE:
<221> NAME/KEY: misc_feature
```

-continued

```
<222> LOCATION: 17
<223> OTHER INFORMATION: T-dabcyl

<400> SEQUENCE: 1
gctagccacc gctagctcca acacgcuagc gguggcuagc                    40

<210> SEQ ID NO 2
<211> LENGTH: 40
<212> TYPE: DNA
<213> ORGANISM: Artificial Sequence
<220> FEATURE:
<223> OTHER INFORMATION: synthesized beacon
<220> FEATURE:
<221> NAME/KEY: misc_feature
<222> LOCATION: 1
<223> OTHER INFORMATION: FAM
<220> FEATURE:
<221> NAME/KEY: misc_feature
<222> LOCATION: 17
<223> OTHER INFORMATION: T-dabcyl

<400> SEQUENCE: 2
gcatgcctcc gcatgctcca acacgcuagc gguggcuagc                    40

<210> SEQ ID NO 3
<211> LENGTH: 40
<212> TYPE: DNA
<213> ORGANISM: Artificial Sequence
<220> FEATURE:
<223> OTHER INFORMATION: synthesized beacon
<220> FEATURE:
<221> NAME/KEY: misc_feature
<222> LOCATION: 1
<223> OTHER INFORMATION: FAM
<220> FEATURE:
<221> NAME/KEY: misc_feature
<222> LOCATION: 17
<223> OTHER INFORMATION: T-dabcyl

<400> SEQUENCE: 3
gctatccacc gatagctcca acacgcuagc gguggcuagc                    40

<210> SEQ ID NO 4
<211> LENGTH: 40
<212> TYPE: DNA
<213> ORGANISM: Artificial Sequence
<220> FEATURE:
<223> OTHER INFORMATION: synthesized beacon
<220> FEATURE:
<221> NAME/KEY: misc_feature
<222> LOCATION: 1
<223> OTHER INFORMATION: FAM
<220> FEATURE:
<221> NAME/KEY: misc_feature
<222> LOCATION: 17
<223> OTHER INFORMATION: T-dabcyl

<400> SEQUENCE: 4
gcttgccacc gcaagctcca acacgcuagc gguggcuagc                    40

<210> SEQ ID NO 5
<211> LENGTH: 42
<212> TYPE: DNA
<213> ORGANISM: Artificial Sequence
<220> FEATURE:
<223> OTHER INFORMATION: synthesized beacon
<220> FEATURE:
<221> NAME/KEY: misc_feature
<222> LOCATION: 1
<223> OTHER INFORMATION: FAM
<220> FEATURE:
```

```
<221> NAME/KEY: misc_feature
<222> LOCATION: 19
<223> OTHER INFORMATION: T-dabcyl

<400> SEQUENCE: 5
gctagccaaa acgctagctc caacacgcua gcgguggcua gc                          42

<210> SEQ ID NO 6
<211> LENGTH: 6
<212> TYPE: PRT
<213> ORGANISM: Artificial Sequence
<220> FEATURE:
<223> OTHER INFORMATION: synthesized cyclic peptide
<220> FEATURE:
<221> NAME/KEY: MOD_RES
<222> LOCATION: 3
<223> OTHER INFORMATION: deoxy-Tryptophan

<400> SEQUENCE: 6

Phe Cys Trp Arg Cys Lys
 1               5

<210> SEQ ID NO 7
<211> LENGTH: 55
<212> TYPE: PRT
<213> ORGANISM: HIV
<220> FEATURE:
<221> NAME/KEY: ZN_FING
<222> LOCATION: (15)...(28)
<223> OTHER INFORMATION: ZINC FINGER
<220> FEATURE:
<221> NAME/KEY: ZN_FING
<222> LOCATION: (36)...(49)
<223> OTHER INFORMATION: ZINC FINGER

<400> SEQUENCE: 7

Met Gln Lys Gly Asn Phe Arg Asn Gln Arg Lys Thr Val Lys Cys Phe
 1               5                  10                  15

Asn Cys Gly Lys Glu Gly His Ile Ala Lys Asn Cys Arg Ala Pro Arg
             20                  25                  30

Lys Lys Gly Cys Trp Lys Cys Gly Lys Glu Gly His Gln Met Lys Asp
         35                  40                  45

Cys Thr Glu Arg Gln Ala Asn
     50                  55

<210> SEQ ID NO 8
<211> LENGTH: 154
<212> TYPE: RNA
<213> ORGANISM: HIV

<400> SEQUENCE: 8
ggagcucucu cgacgcagga cucggcuugc ugaagcgcgc acggcaagag gcgaggggcg      60
gcgacuggug aguacgccaa aaauuuugac uagcggaggc uagaaggaga gagaugggug     120
cgagagcguc aguauuaagc gggggagaau uaga                                 154

<210> SEQ ID NO 9
<211> LENGTH: 40
<212> TYPE: DNA
<213> ORGANISM: Artificial Sequence
<220> FEATURE:
<223> OTHER INFORMATION: synthesized chimeric fluorescent beacon
<220> FEATURE:
<221> NAME/KEY: misc_feature
<222> LOCATION: 1
<223> OTHER INFORMATION: fluorophore
<220> FEATURE:
```

```
-continued

<221> NAME/KEY: misc_feature
<222> LOCATION: 17
<223> OTHER INFORMATION: quencher

<400> SEQUENCE: 9
gctagccacc gctagctcca acacgcuagc gguggcuagc                    40
```